(12) United States Patent
Duan et al.

(10) Patent No.: US 12,383,627 B2
(45) Date of Patent: Aug. 12, 2025

(54) ANTIMICROBIAL SCAFFOLDS

(71) Applicant: BOARD OF REGENTS OF THE UNIVERSITY OF NEBRASKA, Lincoln, NE (US)

(72) Inventors: Bin Duan, Omaha, NE (US); Mitchell Kuss, Omaha, NE (US); Tammy Kielian, LaVista, NE (US); Amy Aldrich, Omaha, NE (US); Wen Shi, Pappillion, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 728 days.

(21) Appl. No.: 17/431,049

(22) PCT Filed: Mar. 6, 2020

(86) PCT No.: PCT/US2020/021440
§ 371 (c)(1),
(2) Date: Aug. 13, 2021

(87) PCT Pub. No.: WO2020/181205
PCT Pub. Date: Sep. 10, 2020

(65) Prior Publication Data
US 2022/0133896 A1 May 5, 2022

Related U.S. Application Data

(60) Provisional application No. 62/814,998, filed on Mar. 7, 2019.

(51) Int. Cl.
| | |
|---|---|
| A61K 47/61 | (2017.01) |
| A61K 31/496 | (2006.01) |
| A61K 38/12 | (2006.01) |
| A61K 47/69 | (2017.01) |
| A61L 27/52 | (2006.01) |
| A61L 27/54 | (2006.01) |
| B33Y 70/10 | (2020.01) |
| B33Y 80/00 | (2015.01) |

(52) U.S. Cl.
CPC ............ *A61K 47/61* (2017.08); *A61K 31/496* (2013.01); *A61K 38/12* (2013.01); *A61K 47/6903* (2017.08); *A61L 27/52* (2013.01); *A61L 27/54* (2013.01); *B33Y 70/10* (2020.01); *B33Y 80/00* (2014.12); *A61L 2300/406* (2013.01)

(58) Field of Classification Search
CPC .. A61K 47/61; A61K 47/6903; A61K 31/496; A61K 38/12; B33Y 80/00; B33Y 70/10; A61L 27/52; A61L 27/54; A61L 2300/406
See application file for complete search history.

(56) References Cited

U.S. PATENT DOCUMENTS

| | | |
|---|---|---|
| 2011/0212501 A1 | 9/2011 | Yoo et al. |
| 2016/0038655 A1* | 2/2016 | Weisman ................ A61L 15/22 425/375 |
| 2016/0095958 A1 | 4/2016 | Grayson et al. |
| 2018/0050130 A1 | 2/2018 | Jiang et al. |
| 2018/0193209 A1 | 7/2018 | Pajamani et al. |

FOREIGN PATENT DOCUMENTS

| | | | |
|---|---|---|---|
| EP | 2340785 A1 | 7/2011 | |
| WO | 2014/075185 A1 | 5/2014 | |
| WO | WO 2019025070 | * 2/2019 | .............. C08J 3/075 |

OTHER PUBLICATIONS

Li, et al., "Degradable Three Dimensional-Printed Polylactic Acid Scaffold with Long-Term Antibacterial Activity" ACS Sustainable Chem. Eng. (2018) 6(2):2047-2054.

Aldrich, et al., "3D Bioprinted Scaffolds Containing Viable Macrophages and Antibiotics Promote Clearance of *Staphylococcus aureus* Craniotomy-Associated Biofilm Infection" ACS Appl. Mater. Interfaces (2019) 11(13): 12298-12307.

Hanke, et al., "Targeting macrophage activation for the prevention and treatment of *Staphylococcus aureus* biofilm Infections" J Immunol. (2013) 190(5):2159-68.

Nowicki, et al., "3D printing of novel osteochondral scaffolds with graded microstructure" Nanotechnology (2016) 27(41):414001.

Rutz, et al., "A multimaterial bioink method for 3D printing tunable, cell-compatible hydrogels" Adv. Mater. (2015) 27(9):1607-14.

Suri, et al., "Solid freeform fabrication of designer scaffolds of hyaluronic acid for nerve tissue engineering" Biomed. Microdevices (2011) 13(6):983-93.

Shim, et al., "Three-dimensional bioprinting of multilayered constructs containing human mesenchymal stromal cells for osteochondral tissue regeneration in the rabbit knee joint" Biofabrication (2016) 8(1):014102.

Duan, et al., "Three-dimensional nanocomposite scaffolds fabricated via selective laser sintering for bone tissue engineering" Acta Biomater. (2010) 6(12):4495-505.

Duan, et al., "Customized Ca-P/PHBV nanocomposite scaffolds for bone tissue engineering: design, fabrication, surface modification and sustained release of growth factor" J. R. Soc. Interface (2010) 7(Suppl 5):S615-29.

Cheatle, et al., "Compartmentalization of immune responses during *Staphylococcus aureus* cranial bone flap Infection" Am. J. Pathol. (2013) 183(2):450-8.

Wang, et al., "Effects of Hydroxyapatite and Hypoxia on Chondrogenesis and Hypertrophy in 3D Bioprinted ADMSC aden Constructs" ACS Biomater. Sci. Eng. (2017) 3(5):826-835.

Kuss, et al., "Prevascularization of 3D printed bone scaffolds by bioactive hydrogels and cell co-culture" J. Biomed. Mater. Res. B Appl. Biomater. (2018) 106(5):1788-1798.

(Continued)

*Primary Examiner* — Shirley V Gembeh
(74) *Attorney, Agent, or Firm* — Robert C. Netter, Jr.; Dann, Dorfman, Herrell & Skillman

(57) ABSTRACT

Three-dimensional printed antibiotic scaffolds are provided as well as methods of use thereof and methods of making.

42 Claims, 18 Drawing Sheets

(56) References Cited

OTHER PUBLICATIONS

Heim, et al., "Interleukin-10 production by myeloid-derived suppressor cells contributes to bacterial persistence during *Staphylococcus aureus* orthopedic biofilm infection" J. Leukoc. Biol. (2015) 98(6):1003-13.

Heim, et al., "IL-12 promotes myeloid-derived suppressor cell recruitment and bacterial persistence during *Staphylococcus aureus* orthopedic implant infection" J. Immunol. (2015) 194(8):3861-3872.

Heim, et al., "Myeloid-derived suppressor cells contribute to *Staphylococcus aureus* orthopedic biofilm infection" J. Immunol. (2014) 192(8):3778-3792.

Heim, et al., "Heterogeneity of Ly6G+ Ly6C+ Myeloid-Derived Suppressor Cell Infiltrates during *Staphylococcus aureus* Biofilm Infection" Infection and Immunity (2018) 86(12):e00684-18 I.

Arafat, et al., "Biomimetic composite coating on rapid prototyped scaffolds for bone tissue engineering" Acta Biomater. (2011) 7(2):809-20.

Lin, et al., "Three-dimensional plotted alginate fibers embedded with diclofenac and bone cells coated with chitosan for bone regeneration during inflammation" J. Biomed. Mater. Res. (2018) 106(6):1511-1521.

\* cited by examiner

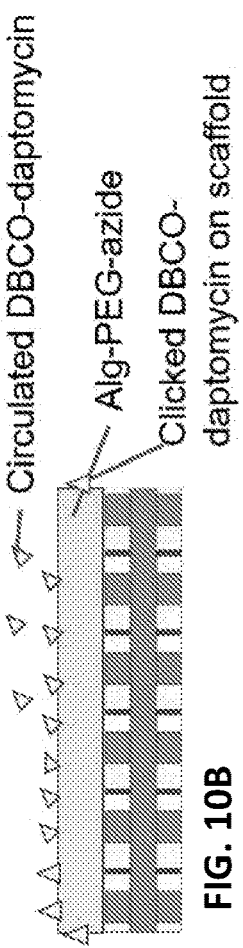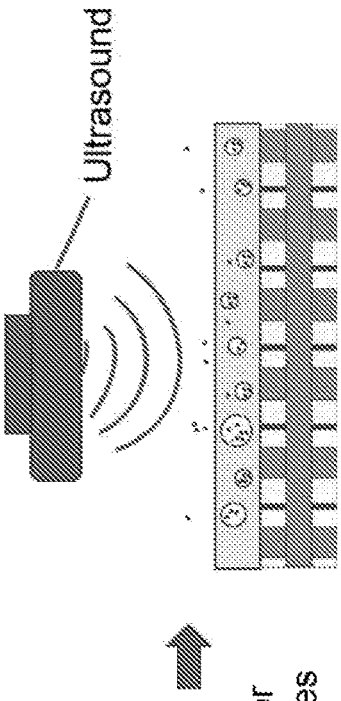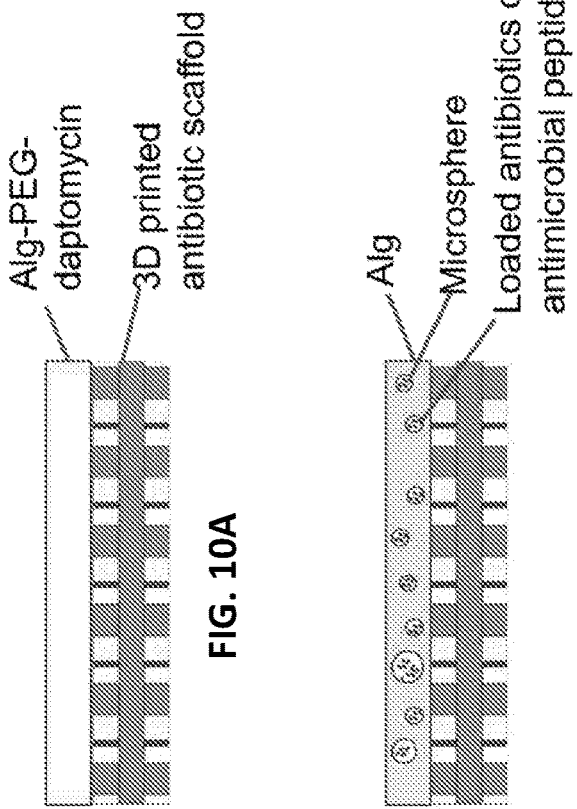
FIG. 10A
FIG. 10B
FIG. 10C

ANTIMICROBIAL SCAFFOLDS

This application is a § 371 application of PCT/US2020/021440, filed Mar. 6, 2020, which claims priority under 35 U.S.C. § 119 (e) to U.S. Provisional Patent Application No. 62/814,998, filed Mar. 7, 2019. The foregoing applications are incorporated by reference herein.

This invention was made with government support under Grant No. NS107369 awarded by National Institutes of Health/National Institute of Neurological Disorders and Stroke. The government has certain rights in the invention

FIELD OF THE INVENTION

This application relates to the fields of 3D printed structures. More specifically, this invention provides antimicrobial 3D printed scaffolds for inhibiting infections associated with craniotomies and methods of synthesizing the same.

BACKGROUND OF THE INVENTION

Several publications and patent documents are cited throughout the specification in order to describe the state of the art to which this invention pertains. Each of these citations is incorporated herein by reference as though set forth in full.

Battlefield case fatality rates (CFR) have declined steadily throughout the twentieth century, from 19.1% among all wounded in WWII, to 15.8% in Vietnam, and 9.4% in Operation Iraqi Freedom and Operation Enduring Freedom (OIF and OEF, respectively) (Blyth, et al. (2015) J. Trauma Acute Care Surg. 79(4 Suppl 2):S227-235; Holcomb, et al. (2006) J. Trauma. 60(2):397-401). The frequency of head wounds during OIF/OEF was dramatically increased compared to earlier conflicts, with most injuries caused by explosives (79%), of which 38% were improvised explosive devices (IEDs) (Owens, et al. (2008) J. Trauma. 64(2):295-299). Traumatic brain injury (TBI) has been estimated to account for up to one-third of combat-related injuries on today's battlefield (Pavlicevic, et al. (2017) J. Craniomaxillofac. Surg., 45(2):312-318; Meyer, et al. (2008) J. Trauma Nurs., 15(4):185-189). Indeed, during OIF and OEF, at least 8,089 TBIs were recorded from IEDs, many of which required life-saving decompressive craniectomy (Ling, et al. (2010) Annu. Rev. Med., 61:457-468). Decompressive craniectomy refers to the surgical removal of a portion of the skull following TBI (or other head-related injuries such as stroke or cranial bleeding) to control subsequent brain edema and prevent death (Stiver, S. I. (2009) Neurosurg. Focus., 26(6):E7). Upon removal, the bone fragment (or bone flap) is typically cryopreserved until future replacement once brain edema has subsided. A surge in decompressive craniectomies has been observed in the last decade, due to reported benefits in the setting of failed medical treatment for intracranial hypertension secondary to TBI and stroke (Hutchinson, et al. (2006) Acta Neurochir. Suppl., 96:17-20; Vahedi, et al. (2007) Stroke 38(9):2506-2517).

A craniotomy refers to the temporary removal of a skull fragment to access the brain, such as during tumor resection or epilepsy treatment, which is replaced intra-operatively. The incidence of infection after craniotomy/craniectomy ranges from 0.8-12% in the modern surgical era, with approximately half attributed to *Staphylococcus aureus* (*S. aureus*), which forms a biofilm on the native bone (McClelland, et al. (2007) Clin. Infect. Dis., 45(1):55-59; Chiang, et al. (2011) J. Neurosurg., 114(6):1746-1754). In patients with cranial defects resulting from combat-related injuries, infection can be assumed, with *S. aureus* among the more prevalent pathogens leading to biofilm formation (Stephens, et al. (2010) Neurosurg. Focus, 28(5):E3). Several factors have been identified that increase the risk for infectious complications after craniotomy, including the presence of another infection, number of operations, cerebrospinal fluid (CSF) leakage, extent of CSF drainage, and venous sinus entry. It has been proposed that CSF leakage promotes the retrograde movement of bacteria, resulting in intracranial infection, which increases intracranial pressure and further CSF leakage, perpetuating a vicious cycle (Fang, et al. (2017) Am. J. Infect. Control 45(11):e123-e134).

Historically, the standard-of-care for managing bone flap infection following craniotomy has been intra-operative debridement of the affected tissue and bone flap removal, whereupon after a prolonged course of antibiotic treatment, a cranioplasty is performed. However, some studies have reported successful regimens for salvaging infected bone flaps, which include aggressive debridement of the surgical site, scrubbing and soaking the bone flap in povidone-iodine or other antiseptics, and in some instances indwelling antibiotic irrigations systems have been used to bathe the bone flap in antibiotics upon reinsertion (Widdel, et al. (2009) J. Neurosurg. Pediatr., 4(4):378-382; Auguste, et al. (2006) J. Neurosurg., 105(4):640-644; Bruce, et al. (2003) J. Neurosurg., 98(6):1203-1207; Wallace, et al. (2018) Neurosurg. Rev., 41(4):1071-1077). In all of these studies, patients received intravenous (i.v.) antibiotics on average for one week followed by a longer duration of oral antibiotics (i.e., 2-3 months) (Widdel, et al. (2009) J. Neurosurg. Pediatr., 4(4):378-382; Auguste, et al. (2006) J. Neurosurg., 105(4): 640-644; Bruce, et al. (2003) J. Neurosurg., 98(6):1203-1207; Wallace, et al. (2018) Neurosurg. Rev., 41(4):1071-1077). Although these studies have shown good efficacy in preventing infection recurrence, they report small sample sizes (i.e., <14 subjects) and have not yet been adapted into mainstream clinical practice.

In instances where the infected bone flap cannot be salvaged, patients are typically subjected to at least two additional surgeries. The first is to remove the infected bone, and after a variable period of antibiotic treatment that can last for weeks to months, a second surgery occurs to seal the cranial cavity with an alloplastic prosthesis or autologous bone graft (Baumeister, et al. (2008) Plast. Reconstr. Surg., 122(6):195e-208e). Prolonged absence of the skull flap during antibiotic treatment can lead to "syndrome of the trephined" in approximately 13% of patients, which can include headache, seizures, mood imbalances, and behavioral disturbances (Honeybul, et al. (2011) J. Neurotrauma 28(6):929-935). Treatment of trephine syndrome is replacement of the original bone flap or synthetic device (Sinclair, et al. (2010) Radiographics 30(2):461-482; Yang, et al. (2008) Acta Neurochir 150(12):1241-1248). However, replacement cannot occur until convincing evidence exists that any residual infection has been eliminated, and some patients experience lingering cognitive impairment. Although less common, patients with craniotomy/craniectomy infections can experience chronic seizures and focal neurological deficits (Bhaskar, et al. (2014) World Neurosurg., 82(3-4):e531-e534). Despite the extensive steps taken both pre- and post-operatively to prevent infectious complications following craniotomy, including surgical scrub techniques, peri-operative antibiotics, post-operative wound care, and discontinuation of wound healing retardant medications, infections still occur and some require the bone flap to be discarded. Improved methods for preventing microbial infections after a craniotomy/craniectomy are clearly needed.

SUMMARY OF THE INVENTION

In accordance with the instant invention, three-dimensional antimicrobial, particularly antibacterial, scaffolds are provided. The scaffolds may be used for implantation into cranial cavities, such as those created during a craniotomy or craniectomy. Generally, the scaffold comprises at least one biocompatible material (e.g., polymer) and at least one antibiotic, antimicrobial peptide, and/or cytokine and comprises a coating, such as a hydrogel. In certain embodiments, the scaffold comprises a hydrophobic polymer (e.g., polycaprolactone) and a hydrophilic polymer (e.g., hyaluronic acid and/or gelatin). In certain embodiments, the hydrophobic polymer comprises a hydrophobic antibiotic (e.g., rifampin) and the hydrophilic polymer comprises a hydrophilic antibiotic (e.g., daptomycin). The scaffolds of the instant invention may be mineralized and/or comprise hydroxyapatite (e.g., hydroxyapatite nanocrystals) and/or may be crosslinked. The hydrogels of the scaffolds of the instant invention may comprise gelatin and/or alginate, optionally hyaluronic acid. The hydrogels of the scaffolds of the instant invention may comprise antimicrobials (e.g., antibiotics or antimicrobial peptides), cytokines (e.g., pro-inflammatory cytokine (e.g., macrophage colony stimulating factor and/or IFN-γ), and/or macrophage (e.g., autologous or allogenic macrophage, which are optionally activated and/or pro-inflammatory). The antimicrobials, cytokines, and/or macrophage may be contained within microspheres within the hydrogel. The antimicrobials and/or cytokines may be covalently attached to the hydrogel, optionally via a linker. The hydrogels of the scaffolds of the instant invention may also comprise covalently attached azide functional groups, optionally via a linker. The scaffolds of the instant invention may be contained within a composition comprising a pharmaceutically acceptable carrier.

In accordance with another aspect of the instant invention, methods for synthesizing the scaffold of the instant invention are provided. In certain embodiments, the methods comprise printing and/or trimming the scaffold into a shape to fit a cranial cavity of a subject to be treated. The method may further comprise first obtaining a computed tomography scan of the cranial cavity in order to generate a model for the scaffold.

In accordance with another aspect of the instant invention, methods of treating, inhibiting, and/or preventing a bacterial infection associated with a craniotomy or craniectomy in a subject are provided. The bacterial infection may comprise a biofilm. The methods comprise inserting or implanting a scaffold of the instant invention into a cranial cavity of the subject. The method may further comprise locally and/or systemically administering an antibiotic to the subject. When the scaffold comprises microspheres, the method may further comprise applying or administering ultrasound to the scaffold implanted in the subject. The methods may further comprise printing and/or trimming the scaffold into a shape to fit a cranial cavity of a subject. The method may further comprise first obtaining a computed tomography scan of the cranial cavity in order to generate a model for the scaffold.

BRIEF DESCRIPTION OF THE DRAWINGS

FIG. 2A: A polycaprolactone (PCL) (polyester)/hydroxyapatite (HAp) slurry was used to generate multiple PCL/HAp frames in each layer throughout the construct. Another printing head deposited hyaluronic acid (HA) and gelatin-based hydrogels between the PCL/HAp frames. Rifampin was incorporated in the PCL/HAp slurry and daptomycin was added to the HA/Gel hydrogel. Both low (~0.6 µg and 1.6 µg rifampin and daptomycin per mg scaffold, respectively) and high (~16 µg and 18 µg rifampin and daptomycin per mg scaffold, respectively) were examined. Once the antibiotic scaffold was dried, viable macrophages were printed on the surface in a HA/Gel hydrogel matrix and immediately implanted into mice. FIG. 2B: Efficacy of 3D bioprinted scaffolds to kill a lawn of *S. aureus* when used fresh or after incubation in PBS for 7 or 14 days to simulate antibiotic release in vivo. FIG. 2C: Quantitation of antibiotic release profile from 3D printed scaffolds over the course of 14 days in vitro. FIG. 2D: Scanning electron microscopy image of a 3D printed antibiotic scaffold depicting the lattice patterning (80× magnification).

FIG. 4A: Schematic depicting the paradigm used to assess the treatment efficacy of 3D bioprinted scaffolds. FIG. 4B: 3D antibiotic scaffolds (daptomycin+rifampin) were inserted at day 7 after *S. aureus* craniotomy infection, whereupon BBB permeability was assessed 3 or 7 days later using Evan's blue. Results are representative of 5 mice per group.

FIG. 6A: Schematic depicting the experimental paradigm to assess the ability of 3D bioprinted scaffolds to prevent S. aureus craniotomy infection. FIG. 6B: 3D bioprinted scaffolds+antibiotics (daptomycin+rifampin) were placed at the time of craniotomy, whereupon mice (n=5 per group) where challenged 1 day later with $10^5$-$10^7$ CFU live S. aureus at the surgical site. Bacterial burdens were determined 7 days later. Results were analyzed by an unpaired Student's t-test with Welch's correction (*, p<0.05).

FIG. 10A provides a schematic of alginate-PEG-daptomycin printed onto antibiotic scaffolds. FIG. 10B provides a schematic of alginate-PEG-azide printed onto antibiotic scaffolds with DBCO-daptomycin administrated systematically. FIG. 10C provides a schematic of microspheres loaded with antibiotics or antimicrobial peptides incorporated into alginate. The alginate-microspheres can be 3D printed onto the 3D antibiotic scaffolds. Application of ultrasound disrupts the ionically cross-linked alginate hydrogels and induce the release of loaded antibiotics from the microspheres.

DETAILED DESCRIPTION OF THE INVENTION

Figure 1A:
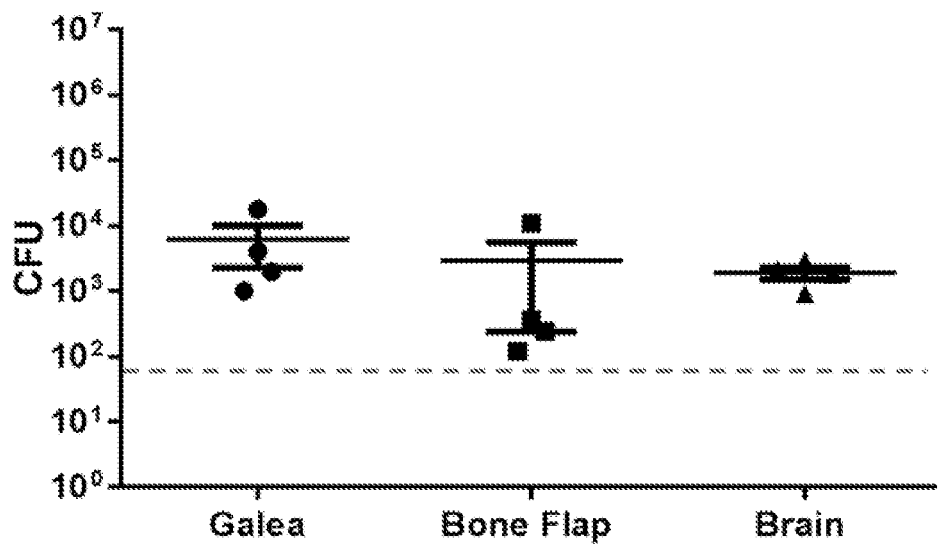
FIGS. 1A and 1B show that craniotomy-associated infections are persistent and recalcitrant to systemic antibiotics. *S. aureus* craniotomy infection was established in C57BL/6 mice (n=5 per group) and animals were sacrificed 9 months later to quantify bacterial persistence in the galea, brain, and bone flap (FIG. 1A). Mice received systemic antibiotics (Abx; daptomycin and rifampin, once/daily) or vehicle (PBS) beginning at day 7 post-infection and continuing for one week, whereupon mice were sacrificed to determine *S. aureus* titers (FIG. 1B). Results are expressed as the number of colony forming units (CFU) per region.

A craniotomy involves the removal of a skull fragment to access the brain, such as during tumor or epilepsy surgery, which is immediately replaced intra-operatively. The infection incidence after craniotomy ranges from 0.8-12% (Bhaskar, et al. (2014) World Neurosurg., 82(3-4):e531-534), with an alarming frequency caused by methicillin-resistant S. aureus (MRSA), which forms a biofilm on the native bone (McClelland, et al. (2007) Clin Infect Dis., 45(1):55-59; Blumenkopf, et al. (1987) J Neurosurg., 66(1): 96-101; Chiang, et al. (2011) J Neurosurg., 114(6):1746-1754). Biofilms are complex bacterial communities that are difficult to treat due to their metabolic dormancy. Reduced metabolic activity affords biofilm-associated bacteria resistance to antibiotic action. However, when biofilms disperse organisms regain their metabolic activity and become sensitive to the same antibiotics (Scherr, et al. (2014) Front Immunol., 5:37; Otto, M. (2008) Curr Top Microbiol Immunol., 322:207-228). To mitigate infectious complications following craniotomy, a 3D bioprinted bone scaffold was engineered to harness the potent antibacterial activity of macrophages together with antibiotics using a mouse S. aureus craniotomy-associated biofilm model that establishes persistent infection on the bone flap, subcutaneous galea, and brain. The 3D scaffold contained rifampin and daptomycin printed in a composite slurry, with viable macrophages incorporated into a hydrogel-based bioink, which was assessed for both the treatment and prevention of craniotomy-associated infections in the mouse model. For the treatment paradigm, the bone flap was removed at day 7 post-infection after a mature biofilm had formed, and replaced with a 3D printed antibiotic scaffold, with or without macrophage incorporation. Bacterial burdens in the galea and brain were reduced by at least 100-fold at early time points, which was potentiated by bioprinting viable macrophages into the 3D antibiotic scaffold. A prevention paradigm, where scaffolds were placed at the time of surgery and challenged with S. aureus one day later at the surgical site, was also examined. The 3D bioprinted scaffold represents an effective treatment modality, since it delivers therapeutic antibiotic levels more rapidly than systemic administration, based on its proximity to the infection site. In addition, the incorporation of viable macrophages into the 3D scaffold is an important advance, which demonstrated improved therapeutic benefit for the treatment of established biofilms that represent the most clinically challenging scenario.

Herein, the utility of a 3D bioprinted bone scaffold (also referred to herein as 3D antibiotic scaffold, 3D printed scaffold, and 3D bioprinted scaffold) is shown for sustained local antibiotic delivery in combination with the incorporation of immune cells to augment bacterial clearance. This study utilized a mouse model of S. aureus craniotomy-associated biofilm, which mimics craniotomy/craniectomy-related infections in humans, based on ultrastructural features of the biofilm, magnetic resonance imaging (MRI) presentation, and persistence (Cheatle, et al. (2013) Am. J. Pathol., 183(2):450-458). A 3D printed bone scaffold was developed to prevent or treat these infections by incorporating sustained-release antibiotics into the scaffold in combination with macrophages that possess potent anti-microbial activity. The introduction of exogenous macrophages into sites of S. aureus biofilm infection is capable of partially reducing bacterial burdens by promoting biofilm dispersal (Hanke, et al. (2013) J. Immunol., 190(5):2159-2168). Biofilms are bacterial communities encased in a self-produced matrix composed of extracellular DNA, polysaccharides, and proteins that are difficult to treat with antibiotics based on their metabolic dormancy (Otto, M. (2008) Curr. Top. Microbiol. Immunol., 322:207-228). Once macrophage-mediated biofilm dispersal is initiated, bacteria become antibiotic-sensitive, since most currently available antibiotics rely on active cell division and protein synthesis, both of which are limited in intact biofilms. Nevertheless, additional factors can influence the metabolic state of bacteria (i.e., oxygen and nutrient availability) and their potential to maintain antibiotic recalcitrance following biofilm dispersal must also be considered (Lewis, K. (2007) Nat. Rev. Microbiol., 5(1):48-56). Another complication of craniotomy-associated infection is recurrence, since residual biofilm remains after the infected bone flap is removed. The 3D bioprinted antibiotic scaffold of the instant invention features sustained antibiotic release directed to the site of infection, which was magnified by the presence of bioprinted macrophages that presumably facilitated biofilm dispersal, effectively transforming dormant biofilm-associated bacteria into metabolically active cells that are sensitive to antibiotic action.

In accordance with the instant invention, implantable 3D printed scaffolds are provided (also referred to herein as 3D bioprinted bone scaffolds, 3D antibiotic scaffolds, and 3D bioprinted scaffolds). In certain embodiments, the 3D printed scaffold is a biomimetic (e.g., of the skull). The 3D printed scaffolds of the instant invention can be printed to the desired size and/or shape. The 3D printed scaffolds can also be trimmed or cut after production to the desired size and/or shape. For example, the 3D printed scaffold may be printed as a patient-specific product or the 3D printed scaffold may be produced as an off-the-shelf product which is later trimmed and/or cut for a specific patient's needs. In certain embodiments, the 3D printed scaffold is designed to fit and/or be implanted into a cranial cavity, such as after a craniotomy/craniectomy surgery. For example, the shape of the 3D printed scaffold may be determined by scanning the cranial cavity (e.g., by a computed tomography (CT) scan). Methods of 3D printing implantable scaffolds are known in the art (see, e.g., Nowicki, et al. (2016) Nanotechnology 27:414001; Rutz, et al. (2015) Advanced Materials 27:1607-1614; Suri, et al. (2011) Biomed Microdevices 13:983-993; Shim, et al. (2016) Biofabrication 8:014102; Duan, et al. (2010) Acta Biomater., 6(12):4495-4505; Duan, et al. (2010) J. R. Soc. Interface., 7 Suppl 5:S615-629, each of which is incorporated by reference herein). The 3D printed scaffolds may be printed with a high-resolution 3D printer (e.g., a 3D-Bioplotter® Manufacturer Series (envisontec, Dearborn, MI)).

The 3D printed scaffolds of the instant invention can be of any desired size. In certain embodiments, the 3D printed scaffold has a thickness of less than about 15 mm, less than about 10 mm, less than about 8 mm, less than about 5 mm, or less than about 3 mm. In a particular embodiment, the 3D printed scaffolds have a thickness of about 0.5 mm to about 10 mm, about 0.5 mm to about 5 mm, about 0.5 mm to about 3 mm, or about 1 mm to about 3 mm.

In certain embodiments, the 3D printed scaffold comprises one or more biocompatible materials. In certain embodiments, the 3D printed scaffold comprises one or more FDA approved biocompatible materials. In certain embodiments, the 3D printed scaffold comprises a single biocompatible material. In certain embodiments, the 3D printed scaffold comprises more than one biocompatible material. For example, the 3D printed scaffold may comprise layers of different biocompatible materials. The 3D printed scaffold may comprise interlaced or interwoven strands of one or more biocompatible materials. For example, a first biocompatible material may be printed in spaced lines and/or frame, then a second biocompatible material may be printed in between the lines and/or frame of the first biocompatible material. In certain embodiments, one of the biocompatible materials is hydrophobic and the other biocompatible material is hydrophilic. In certain embodiments, the 3D printed scaffold is printed in a layer-by-layer manner, optionally wherein the scaffold is rotated 90° at each successive layer to create a grid pattern in the scaffold.

The biocompatible materials of the instant invention include, without limitation: ceramics (e.g., bioceramics), glasses, polymers, composites, glass-ceramics, and metal alloys (e.g., magnesium alloys, titanium alloys, etc.). Suitable materials are described, for example, in Prakasam et al. (J. Funct. Biomater. (2017) 8(4):E44), incorporated herein by reference.

In certain embodiments, the biocompatible material of the 3D printed scaffold is a polymer. The 3D printed scaffold of the instant invention may comprise any biocompatible polymer. The polymer may be biodegradable or non-biodegradable. The polymer may by hydrophobic, hydrophilic, or amphiphilic. In a particular embodiment, the polymer is hydrophobic. In a particular embodiment, the polymer is hydrophilic. In certain embodiments, the 3D printed scaffold comprises at least one hydrophilic polymer and at least one hydrophobic polymer. The polymers of the instant invention may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyper-branched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, polyhydroxybutyrate (PHB), polyhydroxyvalerate (PHV), poly(3-hydroxybutyrate-co-3-hydroxyvalerate) (PHBV), PCL/calcium carbonate, and/or poly(styrene). In certain embodiments, the hydrophobic polymer comprises a polymer selected from the group consisting of polylactic acid (PLA), poly glycolic (PGA), poly(lactic-co-glycolic acid) (PLGA), polyhydroxybutyrate (PHB), polyhydroxyvalerate (PHV), copolymers of PHB and PHV, and polycaprolactone. In a particular embodiment, the hydrophobic polymer comprises polycaprolactone.

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO. In a particular embodiment, the hydrophilic polymer comprises hyaluronic acid and/or gelatin. In certain embodiments, the hydrophilic polymers are methacrylated. In a particular embodiment, the hydrophilic polymer comprises methacrylated hyaluronic acid and/or methacrylated gelatin.

Amphiphilic copolymers or polymer composites may comprise a hydrophilic polymer (e.g., segment) and a hydrophobic polymer (e.g., segment) from those listed above (e.g., gelatin/polyvinyl alcohol (PVA), PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

In certain embodiments, the 3D printed scaffolds of the instant invention are mineralized (e.g., comprise minerals and/or coated with minerals). Mineralization, for example, with hydroxyapatite, can enhance the adhesion of osteogenic precursor cells in vitro and in vivo (Duan, et al., Biomacromolecules (2017) 18:2080-2089). In certain embodiments, the 3D printed scaffolds are coated with and/or comprise Ca, P, and/or O (e.g., immersed in simulated body fluid (SBF) for mineralization (e.g., a solution comprising NaCl, $CaCl_2$, $NaH_2PO_4$, and $NaHCO_3$). In certain embodiments, the 3D printed scaffolds are coated with and/or comprise hydroxyapatite, fluorapatite, or chlorapatite, particularly hydroxyapatite. In a particular embodiment, the 3D printed scaffolds of the instant invention further comprise hydroxyapatite. In certain embodiments, the hydroxyapatite is in the form of nanocrystals. In certain embodiments, the 3D printing materials may comprise hydroxyapatite and a biocompatible material (e.g., polymer). In certain embodiments, the hydroxyapatite is contained within the hydrophobic polymer (e.g., polycaprolactone).

In certain embodiments, the 3D printed scaffolds of the instant invention comprise one or more hydrophobic portions and one or more hydrophilic portions. In certain embodiments, the hydrophobic portion comprises at least one hydrophobic biocompatible material such as a hydrophobic polymer. In certain embodiments, the hydrophilic portion comprises at least one hydrophilic biocompatible material such as a hydrophilic polymer. In certain embodiments, the hydrophobic portion comprises polycaprolactone and hydroxyapatite. In certain embodiments, the hydrophilic portion comprises hyaluronic acid (e.g., methacrylated hyaluronic acid) and gelatin (e.g., methacrylated gelatin). In certain embodiments, the hydrophobic portion (e.g., PCL/hydroxyapatite) is printed in spaced lines and/or a frame, and the hydrophilic portion (e.g., hyaluronic acid/gelatin) is printed in between the lines and/or frame. In certain embodiments, the 3D printed scaffold is printed in a layer-by-layer manner, particularly wherein the scaffold is rotated 90° at each successive layer to create a grid pattern in the scaffold.

In certain embodiments, the 3D scaffolds of the instant invention comprise at least one antimicrobial and/or cytokine. Antimicrobials may include, without limitation, small molecules, peptides, proteins, DNA, RNA, and other known biologic substances. In a particular embodiment, the antimicrobial is a small molecule. In a particular embodiment, the antimicrobial is an antiviral, antifungal, antibiotic or antibacterial, particularly an antibiotic or antimicrobial peptide (e.g., LL-37 or a fragment or derivative thereof (e.g., those provided in Wang et al. (2019) Adv. Exp. Med. Biol., 1117:215-240, incorporated herein by reference). In a particular embodiment, the antimicrobial is a small molecule antibiotic. Examples of antibiotics include, without limitation, beta-lactams (e.g., penicillin, ampicillin, oxacillin, cloxacillin, methicillin, cephalosporin, etc.), monobactams (e.g., aztreonam, tigemonam, nocardicin A, tabtoxin, etc.), carbapenems (e.g., imipenem, meropenem, ertapenem, doripenem, etc.), cephalosporins (e.g., cefdinir, cefaclor, cephalexin, cefixime, cefepime, etc.), carbacephems, cephamycins, macrolides (e.g., erythromycin, clarithromycin, azithromycin etc.), quinolones or fluoroquinolones (e.g., ciprofloxacin, levofloxacin, ofloxacin, delafloxacin, etc.), tetracyclines (e.g., tetracycline, doxycycline etc.), sulfonamides (e.g., sulfamethoxazole, sulfafuraxole, etc.), aminoglycosides (e.g., gentamicin, neomycin, tobramycin, kanamycin, etc.), oxazolidinones (e.g., linezolid, posizolid, tedizolid, radezolid, contezolid, etc.), lipopeptides (e.g., daptomycin), glycylcyclines (e.g., tigecycline), moenomycins, ansamycins (e.g., rifamycins, rifampin), aminocoumarins (e.g., novobiocin), co-trimoxazoles (e.g., trimethoprim and sulfamethoxazole), lincosamides (e.g., clindamycin and lincomycin), polypeptides (e.g., colistin), and glycopeptides (e.g., vancomycin). In certain embodiments, the 3D printed scaffold comprises daptomycin and/or rifampin.

In certain embodiments, if the antimicrobial (e.g., antibiotic) is hydrophobic, it is contained within the hydrophobic portion of the 3D printed scaffold. In certain embodiments, if the antimicrobial (e.g., antibiotic) is hydrophilic, it is contained within the hydrophilic portion of the 3D printed scaffold.

As stated hereinabove, the 3D printed scaffold may comprise at least one cytokine. The cytokine may be pro- or anti-inflammatory. In certain embodiments, the 3D printed scaffold comprises pro-inflammatory cytokines. Pro-inflammatory cytokines include, without limitation: IL-1, IL-6, IL-8, IL-12, IFN-γ, IL-18, TNF, macrophage colony-stimulating factor (M-CSF) and IFN-γ. In certain embodiments, the pro-inflammatory cytokines are M-CSF and/or IFN-γ.

In certain embodiments, the 3D printed scaffold may also further comprise at least one analgesic.

The 3D printed scaffolds of the instant invention may be crosslinked (e.g., to enhance their stability). Crosslinking may be done using a variety of techniques including thermal crosslinking, ionic crosslinking, chemical crosslinking, and photo-crosslinking. For example, the 3D printed scaffolds of the instant invention may be crosslinked with a crosslinker such as, without limitation: formaldehyde, paraformaldehyde, acetaldehyde, glutaraldehyde, a photocrosslinker, genipin, and natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132; incorporated herein by reference). The crosslinker may be a bifunctional, trifunctional, or multifunctional crosslinking reagent. In a particular embodiment, the crosslinker is a photocrosslinker.

In certain embodiments, the 3D printed scaffolds are coated with additional materials to enhance their properties. For example, the 3D printed scaffolds may be coated with a hydrogel, gelatin, alginate, collagen, a proteoglycan, elastin, and/or a glycosaminoglycan (e.g., hyaluronic acid, heparin, chondroitin sulfate, or keratan sulfate). In certain embodiments, the 3D printed scaffolds are coated with the material which enhances the absorption properties. The term "coat" refers to a layer of a substance/material on the surface of a structure. Coatings may, but need not, also impregnate the 3D printed scaffold. Further, while a coating may cover 100% of the 3D printed scaffolds, a coating may also cover less than 100% of the surface of the 3D printed scaffolds (e.g., at least about 75%, at least about 80%, at least about 85%, at least about 90%, at least about 95%, at least about 98%, or more of the surface may be coated). Materials which enhance the absorption properties of the 3D printed scaffolds include, without limitation: gelatin, alginate, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the material is a hydrogel (e.g., a polymer matrix able to retain water in a swollen state). In a particular embodiment, the material comprises gelatin. In a particular embodiment, the material comprises gelatin and hyaluronic acid. In a particular embodiment, the material (e.g., hydrogel) is crosslinked.

In certain embodiments, the coated material further comprises at least one antimicrobial (e.g., antibiotic or antimicrobial peptide). The antimicrobial (e.g., antibiotic) may be the same or different than the one(s) contained within the 3D printed scaffold. The antibiotic (e.g., antibiotic) may be covalently attached to the coated material (e.g., alginate), either directly or through a linker. In certain embodiments, the coating material will comprise unconjugated coating material and coating material covalently attached to the antimicrobial (e.g., antibiotic). Generally, the linker is a chemical moiety comprising a covalent bond or a chain of atoms that covalently attaches the two compounds. The linker can be linked to any synthetically feasible position of the compounds. Exemplary linkers may comprise at least one optionally substituted; saturated or unsaturated; linear, branched or cyclic aliphatic group, an alkyl group, or an optionally substituted aryl group. In a particular embodiment, the linker is an optionally substituted aliphatic or alkyl group. The aliphatic or alkyl group may be unsaturated or saturated and may be substituted with at least one heteroatom (e.g., O, N, or S). In a particular embodiment, the alkyl or aliphatic group comprises about 1 to about 30 carbons (e.g., in the main chain of the alkyl or aliphatic group), which may be substituted with at least one heteroatom (e.g., O, N, or S). In a particular embodiment, the linker comprises polyethylene glycol (e.g., about 1 to about 10 or about 1 to about 5 PEG units). In certain embodiments, the linker comprises click chemistry.

In certain embodiments, the coated material further comprises at least one azide functional group. The azide may be covalently attached to the coated material (e.g., alginate), either directly or through a linker. In certain embodiments, the coating material will comprise unconjugated coating material and coating material covalently attached to the azide. Generally, the linker is a chemical moiety comprising a covalent bond or a chain of atoms that covalently attaches the two compounds. The linker can be linked to any synthetically feasible position of the compounds. Exemplary linkers may comprise at least one optionally substituted; saturated or unsaturated; linear, branched or cyclic aliphatic group, an alkyl group, or an optionally substituted aryl group. In a particular embodiment, the linker is an optionally substituted aliphatic or alkyl group. The aliphatic or alkyl group may be unsaturated or saturated and may be substituted with at least one heteroatom (e.g., O, N, or S). In a particular embodiment, the alkyl or aliphatic group comprises about 1 to about 30 carbons (e.g., in the main chain of the alkyl or aliphatic group), which may be substituted with at least one heteroatom (e.g., O, N, or S). In a particular embodiment, the linker comprises polyethylene glycol (e.g., about 1 to about 10 or about 1 to about 5 PEG units). The 3D printed scaffold of the instant invention comprising the azide group may be loaded (e.g., before implantation) with an antimicrobial (e.g., antibiotic) by contacting the azide-containing coating with an alkyne-conjugated antimicrobial (e.g., antibiotic or antimicrobial peptide). For example, the alkyne-conjugated antimicrobial (e.g., antibiotic) may comprise dibenzocyclooctyne covalently attached (e.g., directly or via a linker) to the antimicrobial (e.g., antibiotic). The alkyne-conjugated antimicrobial (e.g., antibiotic) may be the same or different than the antimicrobial(s) (e.g., antibiotic) contained within the 3D printed scaffold. In certain embodiments, the azide functional group is conjugated to (either directly or through a linker) or contained within the 3D printed scaffold and the alkyne-conjugated antimicrobial (e.g., antibiotic or antimicrobial peptide) is conjugated to the 3D printed scaffold by click chemistry.

In certain embodiments, the coated material further comprises microspheres comprising at least one antimicrobial (e.g., antibiotic) and/or cytokine. The antimicrobial (e.g., antibiotic) and/or cytokines of the microsphere may be the same or different than the one(s) contained within the 3D printed scaffold. In certain embodiments, the microspheres are ultrasound sensitive. In other words, the microspheres are broken, dissolved, and/or fragmented after the application of ultrasound, thereby releasing the encapsulated contents (e.g., antibiotic, antimicrobial peptide, and/or cytokine). The ultrasound may be applied, for example, at a time after which antibiotic release from the 3D scaffold is complete or near complete. In a particular embodiment, the microsphere comprises polymers such as, without limitation, poly(lactic-co-glycolic acid) (PLGA), polycaprolactone (PCL), poly(lactic acid (PLA or PDLA), gelatin, collagen, or chitosan.

The 3D printed scaffolds of the instant invention may further comprise and/or encapsulate cells. In certain embodiments, the 3D printed scaffold further comprises macrophage. In certain embodiments, the cells (e.g., macrophage) are autologous to the subject to be treated with the 3D printed scaffold. The 3D printed scaffold may comprise and/or encapsulate any cell type. In certain embodiments, the cells are immune cells such as, but not limited to, T cells, B cells, NK cells, macrophages, neutrophils, dendritic cells and modified forms of these cells and various combinations thereof. In certain embodiments, the cells are phagocytic. In certain embodiments, the cells are macrophage (e.g., pro-inflammatory macrophage). The cells (e.g., macrophage) may be autologous or allogenic. The cells (e.g., macrophage) may be activated or non-activated. The cells (e.g., macrophage) may be cultured on the 3D printed scaffold (e.g., the cells may be cultured for sufficient time to allow for growth in and/or on the 3D printed scaffold). For example, the cells may be cultured for 1 day, 2 days, 3 days, 4 days, 5 days, or more.

In certain embodiments, the cells (e.g., macrophage) are printed onto the surface of the 3D printed scaffold. For example, the cells (e.g., macrophage) may be printed on the surface of the 3D printed scaffold in a coating as described above (e.g., hydrogel, particularly a hydrogel comprising gelatin and/or hyaluronic acid).

After synthesis, the 3D printed scaffolds may be washed or rinsed in water and/or a desired carrier or buffer (e.g., a pharmaceutically or biologically acceptable carrier). The 3D printed scaffolds may also be stored in a cold solution, lyophilized and/or freeze-dried (e.g., before the addition of cells). Compositions comprising the 3D printed scaffold of the instant invention and at least one pharmaceutically acceptable carrier are also encompassed by the instant invention.

The 3D printed scaffolds of the instant invention may also be sterilized (e.g., before the addition of cells). For example, the 3D printed scaffolds can be sterilized using various methods (e.g., by treating with ethylene oxide gas, gamma irradiation, ultraviolet radiation, or 70% ethanol).

In accordance with another aspect of the instant invention, methods of treating, inhibiting, and/or preventing a microbial or bacterial infection (e.g., biofilm infection) during a craniotomy or craniectomy are provided. In certain embodiments, the method methods of treats, inhibits, and/or prevents a cranial bone flap infection. In certain embodiments, the method methods of treats, inhibits, and/or prevents the recurrence of infection after the surgical removal of an infected cranial bone flap. In certain embodiments, the methods comprise implanting or inserting a 3D printed scaffold of the instant invention into a hole or cavity in the skull of the subject. In certain embodiments, the 3D printed scaffold is implanted or inserted into a hole or cavity in the skull caused by the removal of bone during a craniotomy or craniectomy. The methods of the instant invention may further comprise the removal of a portion of the skull for the insertion or implantation of the 3D printed scaffold. The methods of the instant invention may optionally comprise replacing the cranial bone flap. In certain embodiments, the subject to be treated by the instant methods have undergone a craniotomy or craniectomy (e.g., a depressurization craniotomy or craniectomy) to treat a brain tumor, to treat epilepsy, or to treat a head wound or traumatic brain injury (e.g., military personnel).

The methods of the instant invention may further comprise scanning the hole or cavity in the brain (e.g., by a CT scan) to determine the size and shape of the 3D printed scaffold. The methods may further comprise synthesizing the 3D printed scaffold (e.g., with a high-resolution 3D printer (e.g., 3D-Bioplotter®).

The methods of the instant invention may further comprise the application of transcranial ultrasound to the subject, particularly wherein the 3D printed scaffold comprises antimicrobial (e.g., antibiotic) loaded microspheres (microparticles). The ultrasound may be applied locally to the site of implant of the 3D printed scaffold. The method may comprise more than one application of ultrasound. The ultrasound may be applied at any time after the implant of the 3D printed scaffold (e.g., at least one, day, at least one week, or at least one month after implant).

The methods of the instant invention may further comprise administering at least one antimicrobial (e.g., antibiotic) to the subject. The antimicrobial (e.g., antibiotic) may be the same or different than the one(s) contained within the 3D printed scaffold implanted in the subject. The further antimicrobial (e.g., antibiotic) administered to the subject may be administered systemically (e.g., by injection into the blood stream) or locally (e.g., by injection). In certain embodiments, the antimicrobial (e.g., antibiotic) is an alkyne-conjugated antimicrobial (e.g., antibiotic), particularly wherein the 3D printed scaffold comprises an azide-conjugated coating.

In accordance with another aspect of the instant invention, methods of synthesizing the 3D printed scaffolds described herein are provided. In a particular embodiment, the method comprises 3D printing the scaffolds as described hereinabove (e.g., with a high-resolution 3D printer (e.g., 3D-Bioplotter®)). In a particular embodiment, the method further comprises scanning the skull of the subject to determine the size and shape of the 3D printed scaffold (e.g., by a CT scan).

Definitions

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 4,000, or less than 2,000 Da). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. A "photocrosslinker" refers to a molecule capable of forming a covalent linkage between compounds after photoinduction (e.g., exposure to electromagnetic radiation in the visible and near-visible range). Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent.

The following examples illustrate certain embodiments of the invention. They are not intended to limit the invention in any way.

EXAMPLE 1

Materials and Methods

Generation of 3D Bioprinted Scaffolds Containing Antibiotics and Viable Macrophages 3D printed scaffolds were engineered using a high-resolution 3D bioprinter (3D-Bioplotter® Manufacturer Series, EnvisionTEC; Dearborn, MI). A polycaprolactone (PCL, Mw 80,000, Sigma-Aldrich, St. Louis, MO)/hydroxyapatite (HAp nanocrystals, avg. 100 nm, Berkeley Advanced Biomaterials, Inc.; Berkeley, CA) slurry was used to generate multiple PCL/HAp frames in each layer throughout the construct. Another printing head deposited methacrylated hyaluronic acid (Me-HA, 1,200 kDa, NovaMatrix; Sandvika, Norway) and methacrylated gelatin (Me-Gel, from type B gelatin, Sigma)-based hydrogels between the PCL/HAp frames (Kuss, et al. (2018) J. Biomed. Mater. Res. B Appl. Biomater., 106(5):1788-1798; Wang, ET AL. (2017) ACS Biomater. Sci. Engineer., 3:826-835). An antibiotic cocktail containing both hydrophobic and hydrophilic antibiotics (rifampin and daptomycin, respectively) was incorporated into the scaffold, where rifampin was included in the PCL/HAp slurry and daptomycin was added to the HA/Gel hydrogel (photocrosslinked). The drug components and doses are controllable and in vitro and in vivo pilot studies identified an optimal concentration of 16 µg rifampin and 18 µg daptomycin per mg scaffold (i.e., ~20 mg/ml in the bioinks). The antibiotic scaffold was dried after printing and UV sterilized for 2 hours. For macrophage incorporation, a total of $10^7$ viable bone marrow-derived macrophages were printed on the surface in a HA/Gel hydrogel matrix in L929 supernatant as a source of macrophage colony-stimulating factor (M-CSF) to maximize cell viability. Bone marrow-derived macrophages were prepared (Yamada, et al. (2018) Infect. Immun., 86(7): e00206-18), and approximately $10^4$ macrophages were printed per 3 mm$^2$ scaffold that was inserted into the cranial cavity. For the treatment paradigm, scaffolds were trimmed to size and placed in the space of the voided infected bone flap following tissue debridement, whereupon the skin was sutured closed. In the case of the prevention paradigm, scaffolds were inserted at the time the craniotomy was performed, as described above. The 3D bioprinted implant was approximately 1 mm thick and not malleable following hydration. It was printed in its final shape and trimmed to fill the voided space following removal of the infected bone flap. Structurally, the 3D printed implant is distinct from the attributes of the explanted bone flap in that it is not a solid structure but instead has a lattice configuration.

Antibiotic Release from 3D Bioprinted Scaffolds 3D printed scaffolds (~8 mm in diameter and ~1 mm in thickness) with low (~3.2 µg rifampin and ~3.6 µg daptomycin per mg scaffold) and standard (~16 µg rifampin and ~18 µg daptomycin per mg scaffold) antibiotic doses were immersed in 1 mL sterile PBS and incubated at 37° C. At predetermined time points, the PBS release solution was removed and stored at −80° C. until testing, whereupon fresh PBS was added to scaffolds. The concentration of released rifampin was calculated from the absorbance measured with an UV spectrophotometer at 474 nm (Mohyeldin, et al. (2016) Int. J. Nanomedicine 11:2209-2222). The concentration of released daptomycin was determined using a high performance liquid chromatography (HPLC) system (Agilent Technologies; Santa Clara, CA) with a Poroshell 120 (EC-C18, 2.7 µm) column, and the specific chromatographic conditions were as follows: 0.7 mL/minute flow; injection volume of 20 mL; mobile phase of 35% acetonitrile and 65% PBS (pH 7.4) and detection at 230 nm.

In Vitro Toxicity Testing

Primary human osteoblasts (hOBs) were purchased from Promocell (Heidelberg, Germany) and cultured in DMEM/F12 medium supplemented with 10% FBS and 1% penicillin/streptomycin (all from Invitrogen; Carlsbad, CA) in 5% $CO_2$ at 37° C. Medium was replaced every 2 days and cells were used between passages 4-6.

To assess whether the 3D bioprinted scaffolds exhibited any cytotoxicity, hOBs were seeded at a density of $10^5$ cells per UV sterilized scaffold. Cell viability was examined using a Live/Dead assay (Invitrogen) after 14 days of culture by confocal microscopy (LSM 710, Carl Zeiss) (Kuss, et al. (2018) Acta Biomater., 71:486-495). Quantitative assessments of hOB viability on various scaffold formulations were performed using an MTT assay after 7 and 14 days in culture (Wu et al. (2017) Biofabrication 9(4):044106). To determine whether sustained antibiotic release would negatively affect the brain, the survival of mouse primary mixed neuron-glial cultures was examined. Mixed neuron-glial cultures were prepared from neonatal C57BL/6 mice (Esen, et al. (2007) J. Neuroinflammation 4:10). For toxicity assessments, 3D printed antibiotic scaffolds (8 mm diameter) were incubated in media to release antibiotics for up to 14 days. At days 1, 7, and 14, conditioned media was collected and mixed neuron-glia cultures were treated with 10-fold dilutions of supernatants for 48 hours, whereupon cell viability was assessed using a lactate dehydrogenase (LDH) assay (Promega; Madison, WI). Both MTT and LDH release assays are widely used as reliable assessments of cell viability and provide complementary information.

Mouse Model of S. aureus Craniotomy-Associated Biofilm Infection

Male and female C57BL/6 mice were purchased from Charles River Laboratories (Wilmington, MA) and were utilized between 8-10 weeks of age. Animals were provided with food and water ad libitum, and housed under 12 hour light/dark cycles. Mice were anesthetized using ketamine/xylazine, and an incision was made in the skin opposite to the side the bone flap (Cheatle, et al. (2013) Am. J. Pathol., 183(2):450-458). A high-speed pneumatic drill was used to create a bone flap (approximately 3 mm in diameter) that was incubated in a broth culture of S. aureus (USA300 LAC13C (Thurlow, et al. (2011) J. Immunol., 186(11):6585-6596)) for 5 minutes to allow for bacterial adherence, rinsed, and immediately reinserted into the skull, whereupon the skin incision was closed by suturing. The procedure results in S. aureus colonization of the bone flap, which ultimately leads to infection persistence in the subcutaneous galea and brain (Cheatle, et al. (2013) Am. J. Pathol., 183(2):450-458). Although great care is taken to preserve the integrity of the dura during the craniotomy procedure in the mouse, damage to the dura may occur. Bacteria are present on both surfaces of the bone flap in the mouse model, which was also observed at the ultrastructural level in a study of a bone flap from a patient with confirmed MRSA infection (Cheatle, et al. (2013) Am. J. Pathol., 183(2):450-458), making the possibility of bacterial translocation into the brain a possibility. For the prevention paradigm, a bone flap was created as described above, but was immediately reinserted, with a 3D scaffold placed on top. The following day, $10^5$-$10^8$ CFU of S. aureus was injected subcutaneously in the area of the scaffold/flap. For the treatment paradigm, infected bone flaps were removed and discarded at day 7 and replaced with 3D bioprinted scaffolds under ketamine/xylazine anesthesia. For systemic antibiotic (Abx) administration, mice received once daily i.p. injections of daptomycin and rifampin (5 and 25 µg/ml, respectively).

Tissue Processing and Bacterial Quantification

At the indicated time points post-infection, mice were sacrificed using an overdose of inhaled isoflurane and transcardially perfused with PBS. The bone flap and scaffold were removed first, followed by the galea, which represents the subcutaneous tissue and associated purulent exudate. Next, the ipsilateral brain hemisphere associated with the infected bone flap was removed and placed in PBS. The bone flap and scaffolds were vortexed in PBS for 30 seconds followed by a 5 minute sonication to dislodge biofilm-associated bacteria. The galea was dissociated in PBS using the blunt end of a plunger from a 3 cc syringe and the brain was homogenized by being pressed through a 70 µm cell strainer using the blunt end of a syringe plunger and rinsed with PBS. Once all of the tissues were processed, an aliquot was removed to quantify bacterial titers. Titers were determined by serial dilutions on TSA plates supplemented with 5% sheep blood (Remel, Lenexa, KS) and are expressed as $Log_{10}$ colony forming units (CFUs). The contralateral hemisphere was examined during initial experiments; however, the degree of bacterial dissemination was low, which precluded an accurate assessment of 3D scaffold efficacy and therefore, was not continued for the remainder of the study.

Flow Cytometry

After aliquots were removed for quantifying S. aureus titers, the galea and brain were further processed for flow cytometry to determine how the 3D bioprinted scaffolds affected leukocyte infiltrates. Briefly, the brain homogenate was incubated in a dissociation buffer containing HBSS, collagenase IV, and DNaseI (both from Sigma-Aldrich) for 20 minutes at 37° C., whereupon 20% FBS was added to stop enzymatic activity followed by centrifugation at 300×g for 10 minutes. The pellet was layered over a 25% Percoll® (GE Healthcare; Marlborough, MA) gradient containing 3% FBS and centrifuged at 520×g for 20 minutes with no brake (LaFrance-Corey, et al. (2011) J. Vis. Exp., 52:2747). The upper myelin layer down to the pellet was discarded, and the pellet was resuspended in PBS and filtered to remove remaining particulate material. The galea sample was also centrifuged and filtered, and cells from both the galea and brain were incubated with TruStain fcX™ (BioLegend; San Diego, CA) to block nonspecific antibody binding to Fc receptors. Cells were then stained with CD11b-FITC, CD45-APC, Ly6G-PE, Ly6C-PerCP-Cy5.5, and F4/80-PE-Cy7

(BioLegend and BD Biosciences; San Diego, CA). Dead cells were excluded using a Live/Dead® Fixable Cell Stain Kit (Invitrogen) according to the manufacturer's instructions. Analysis was performed using BD FACSDiva™ software and results are presented as the percentage of live, CD45+leukocytes. Myeloid-derived suppressor cells (MDSCs) were classified as CD11b$^{high}$Ly6C$^+$Ly6G$^+$F4/80$^-$, neutrophils as CD11b$^{low}$Ly6C$^+$Ly6G$^+$F4/80$^-$, and monocytes Ly6C$^+$Ly6G$^-$CD11b$^+$F4/80$^-$ (Heim et al. (2018) Infect. Immun., 86(12): e00684-18).

Determination of Blood-Brain Barrier (BBB) Integrity

Mice were anesthetized with isoflurane and subsequently administered 100 μl of a solution of 2.0% Evans blue dye in PBS via the retro-orbital vein. Animals were euthanized 60 minutes following Evans blue injection and perfused transcardially with 20 ml of PBS using a peristaltic pump to remove residual dye from the circulation. The brain was immediately removed and imaged to depict the extent of Evan's blue accumulation in the brain parenchyma, reflective of BBB permeability.

Statistical Methods

Significant differences between groups were determined using an unpaired Student's t-test with Welch's correction or a One-way ANOVA with Tukey's multiple comparison test using GraphPad Prism version 6 (La Jolla, CA) where a p-value <0.05 was considered statistically significant.

Results

Persistence of *S. aureus* Craniotomy-Associated Biofilm Infection and Recalcitrance to Systemic Antibiotics A mouse model of *S. aureus* craniotomy-associated infection was used where bacteria colonize both surfaces of the bone flap to establish infection in the subcutaneous galea and brain (Cheatle, et al. (2013) Am. J. Pathol., 183(2):450-458). Both chronicity and recalcitrance to systemic antibiotics are characteristics of biofilms, which was demonstrated in the craniotomy model by the persistence of infection out to 9 months (FIG. 1A) and resistant to systemic rifampin and daptomycin (FIG. 1B), an antibiotic regimen used to treat staphylococcal infections (Saleh-Mghir, et al. (2011) Antimicrob. Agents Chemother., 55(10):4589-4593; Lefebvre, et al. (2010) Int. J. Antimicrob. Agents 36(6):542-544). However, antibiotic accumulation in the CNS following systemic administration is slow due to restriction by the blood-brain barrier (BBB) (Nau, et al. (2010) Clin. Microbiol. Rev., 23(4):858-883). Therefore, a 3D printed scaffold was developed to deliver antibiotics directly at the site of infection using a slow release formulation, in either treatment or prevention paradigms. A second approach was to determine if harnessing the antibacterial activity of macrophages, by incorporation into the 3D printed scaffold, would augment antibiotic action to facilitate *S. aureus* clearance.

Figure 2A:
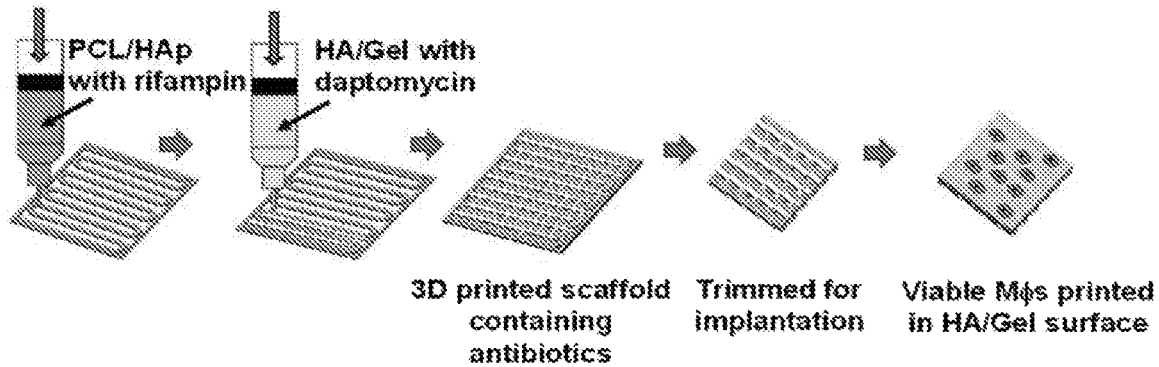
FIGS. 2A-2D show the release profile and bactericidal effect of 3D printed scaffolds containing daptomycin and rifampin.
Figure 2B:
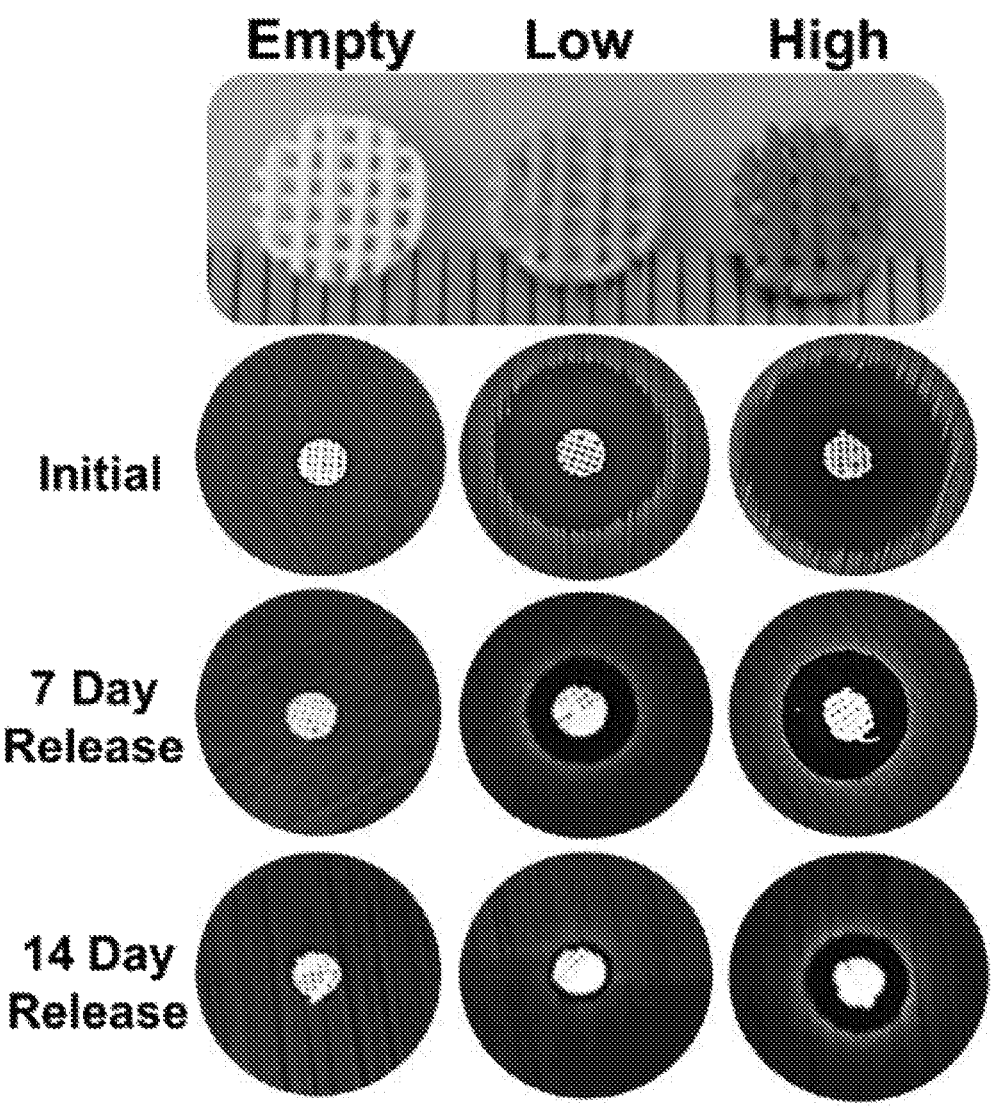
Figure 2C:
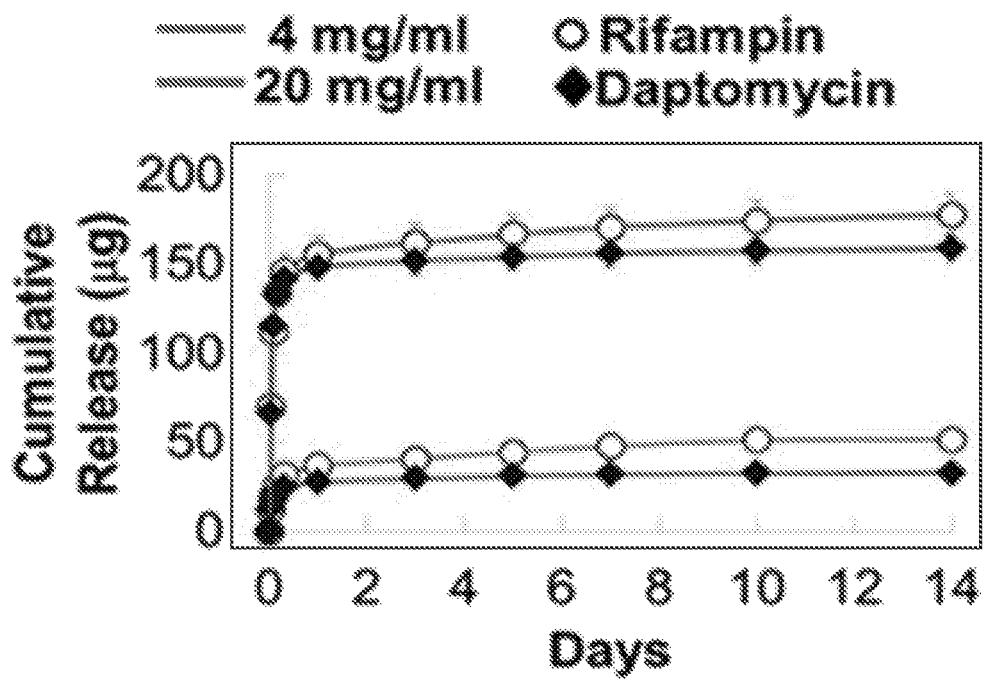
Figure 2D:
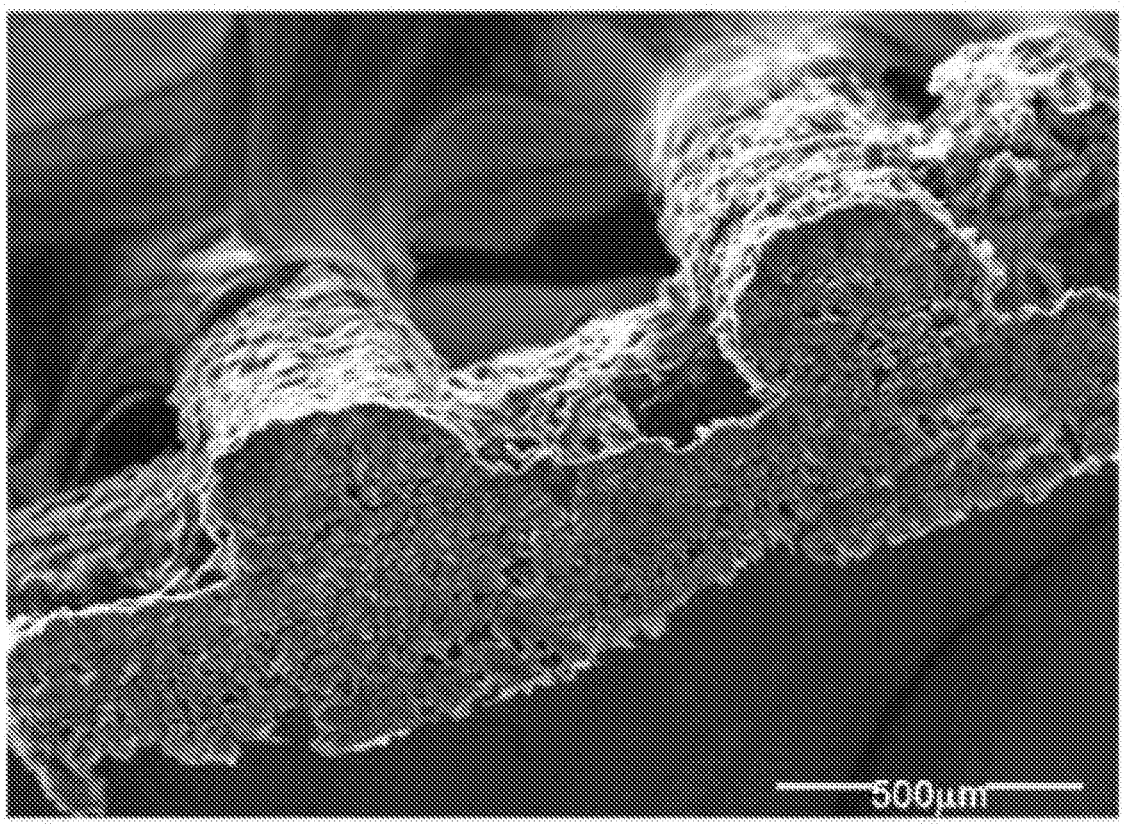

Development of a 3D Bioprinted Scaffold Containing Antibiotics and Viable Macrophages A high-resolution 3D bioprinter was used that can support different materials for printing synthetic bone constructs. The 3D printing parameters, material compositions, and material usage were optimized to guarantee controllability, reproducibility, and quality of the printed scaffolds (Kuss, et al. (2018) J. Biomed. Mater. Res. B Appl. Biomater., 106 (5):1788-1798; Wang, et al. (2017) ACS Biomater. Sci. Engineer., 3:826-835). A PCL/HAp slurry containing rifampin was utilized to generate a PCL/HAp frame in each layer (FIG. 2A). Next, another printing head was used to deposit the Me-HA/Me-Gel hydrogel-based bioink containing daptomycin between the PCL/HAp frame on the same layer. Me-HA/Me-Gel bioinks were further photocrosslinked after 3D printing (Kuss, et al. (2018) J. Biomed. Mater. Res. B Appl. Biomater., 106(5):1788-1798). Incorporation of antibiotics into each printing formulation was based on their solubility properties. Once the antibiotic scaffold was dried and sterilized, viable macrophages were printed on the surface in a HA/Gel hydrogel, and the scaffolds were trimmed to the size of bone flaps for implantation at the craniotomy site (FIG. 2A). The drug components and doses are controllable. Therefore, the studies were initiated by testing scaffolds with low (~3.2 μg rifampin/mg scaffold and ~3.6 μg daptomycin/mg scaffold, respectively) and high (~16 μg rifampin/mg scaffold and ~18 μg daptomycin/mg scaffold, respectively) antibiotic concentrations. Both 3D antibiotic scaffolds demonstrated robust killing of the community-acquired *S. aureus* clinical isolate, USA300 LAC13C (Thurlow, et al. (2011) J. Immunol., 186(11):6585-6596), whereas empty scaffolds had no activity (FIG. 2B). To evaluate the longevity of antibiotic action following release from the bioprinted scaffolds in vitro, scaffolds were incubated in medium for either 7 or 14 days, whereupon they were placed on a lawn of *S. aureus* to determine the extent of bactericidal activity. While both the high and low antibiotic scaffolds inhibited growth following 7 days of release in a dose-dependent manner, the lower concentration was not as effective after 14 days, whereas the high dose scaffold retained antimicrobial activity (FIG. 2B). In vitro kinetic release studies demonstrated that both antibiotics had significant burst release at day 1, with sustained release for at least 14 days, with both antibiotics demonstrating similar release rates (FIG. 2C). Since maximal scaffold efficacy in vivo was envisioned to be achieved by sustained release of high antibiotic concentrations, the 3D bioprinted scaffold harboring high dose antibiotics was used for all subsequent experiments.

Figure 3A:
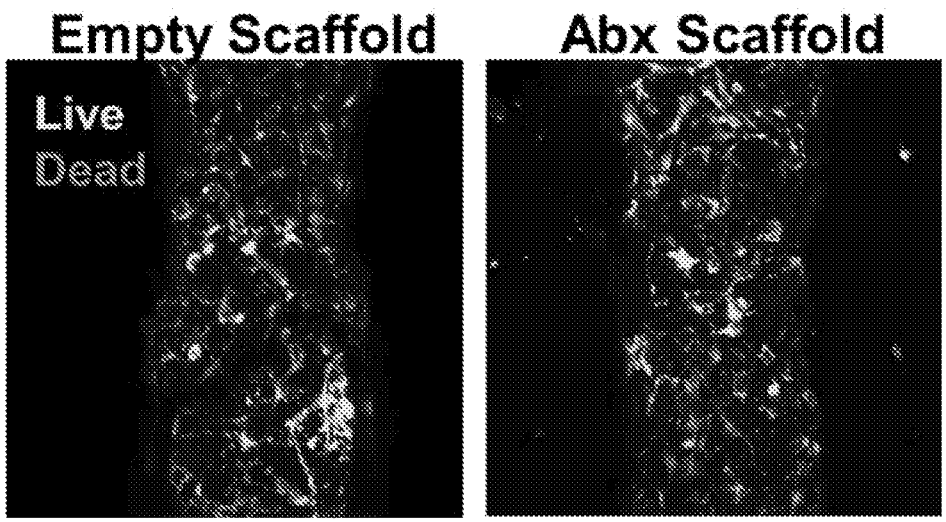
FIGS. 3A-3C show that 3D antibiotic scaffolds are not cytotoxic. Primary human osteoblasts were cultured on 3D antibiotic (Abx) scaffolds in vitro for 7 or 14 days, whereupon osteoblast viability was examined by confocal microscopy (FIG. 3A) and cell survival was demonstrated by MTT assay (FIG. 3B). Survival of primary mouse neuron-glial cultures after exposure to conditioned medium from 3D antibiotic scaffolds incubated for 1-14 days in medium as assessed by LDH release assays (FIG. 3C). Results are reported as the mean±SD of three biological replicates.
Figure 3B:
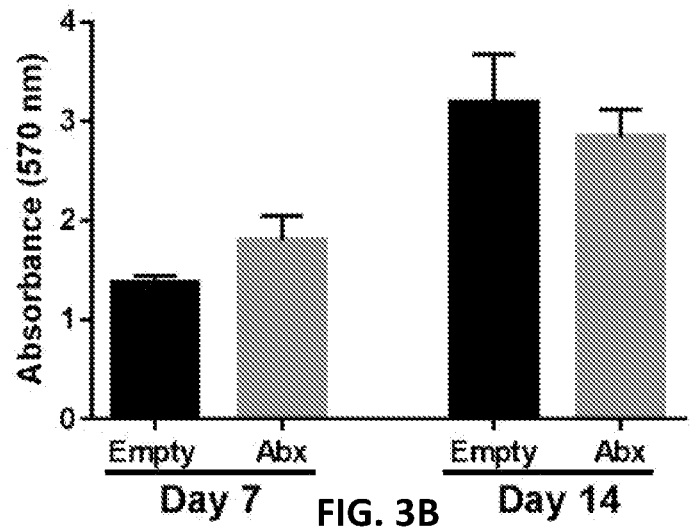
Figure 3C:
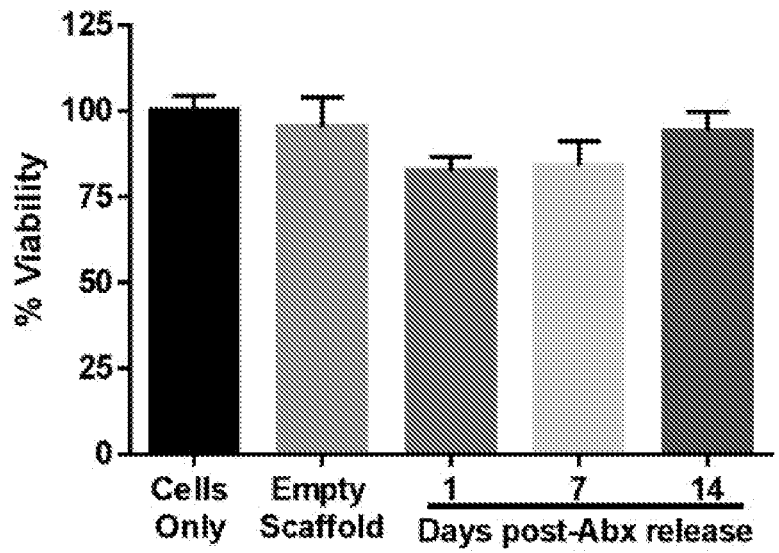

To assess the potential toxicity of 3D bioprinted scaffolds, effects on primary hOBs and mixed neuron-glial cultures were examined. Culture of hOBs on scaffolds for 14 days revealed no evidence of cell death, as determined by a Live/Dead™ assay (FIG. 3A) or MTT assay, where hOB proliferation over time was evident (FIG. 3B). To evaluate potential CNS toxicity, mouse neuron-glial cultures were exposed to medium where antibiotics had been released from the 3D printed scaffold over a 1, 7, or 14 day period. No adverse effects of antibiotic exposure on brain cell viability were observed at any of the concentrations examined (FIG. 3C). Collectively, these results indicate that the 3D bioprinted scaffolds are be well tolerated and safe for in vivo testing.

Figure 1B:
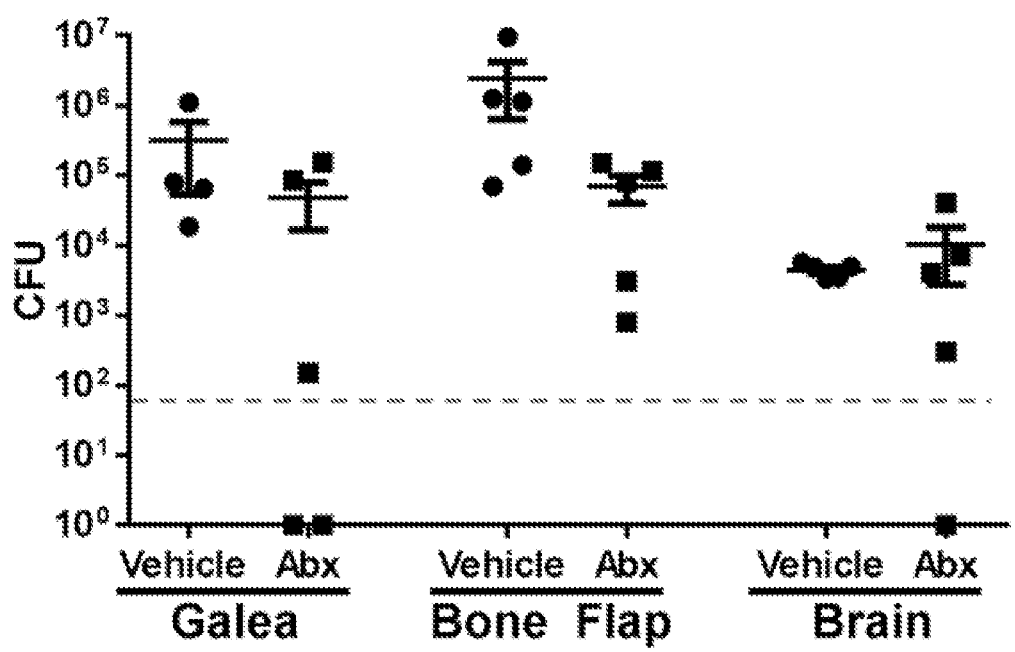
Figure 4A:
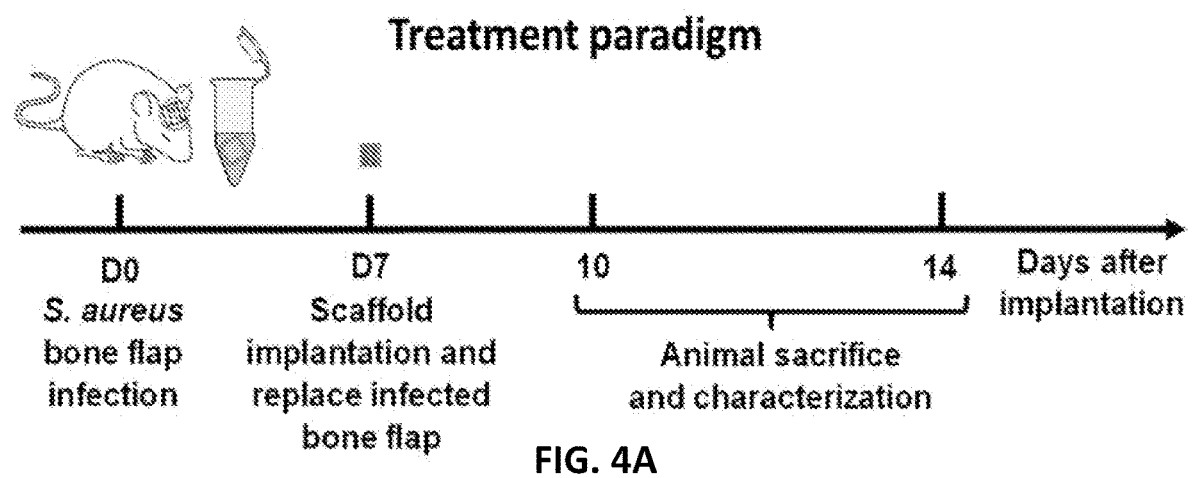
FIGS. 4A and 4B show that 3D antibiotic scaffolds reduce blood-brain barrier (BBB) permeability associated with *S. aureus* craniotomy infection.
Figure 4B:
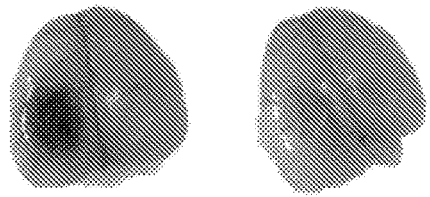
Figure 4B:
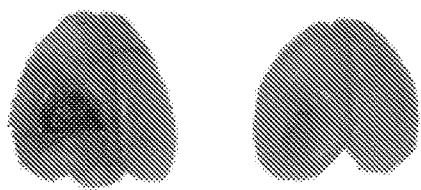

3D Bioprinted Antibiotic Scaffolds Containing Macrophages Promote *S. aureus* Clearance During Craniotomy-Associated Biofilm Infection The treatment of established biofilm infections represents a challenging clinical scenario due to the large bacterial biomass and microdomains of metabolic dormancy (Wood, et al. (2013) Appl. Environ. Microbiol., 79(23):7116-7121; Lewis, et al. (2007) Nat. Rev. Microbiol., 5(1):48-56). To evaluate the efficacy of 3D bioprinted scaffolds against an existing biofilm, infected bone flaps were replaced at day 7 post-infection with 3D bioprinted antibiotic scaffolds or empty scaffolds as a control (FIG. 4A). Treatment was initiated at day 7 post-infection, since bona fide biofilm formation has occurred based on recalcitrance to systemic antibiotics (FIG. 1B). It was first evaluated whether the 3D antibiotic scaffold modulated BBB integrity during infection using Evan's blue. The 3D antibiotic scaffold led to a dramatic reduction in BBB permeability (FIG. 4B), indicating improved outcomes in terms of decreased bacterial burdens and inflammation.

Figure 5A:
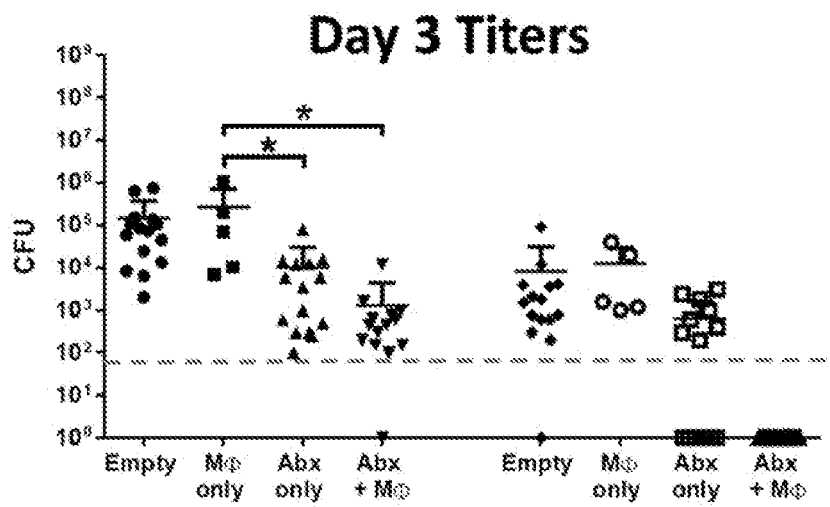
FIGS. 5A-5C show that 3D antibiotic scaffolds reduce bacterial burdens during *S. aureus* craniotomy infection, which is augmented by viable macrophages. 3D bioprinted scaffolds containing antibiotics (Abx) only (daptomycin+rifampin), macrophages (MΦs) only, antibiotics+macrophages, or empty scaffolds were placed at day 7 after *S. aureus* craniotomy infection, whereupon bacterial burdens (FIG. 5A), myeloid-derived suppressor cells (MDSC) (FIG. 5B), and monocyte (FIG. 5C) infiltrates in the galea and brain were determined 3 days later (i.e. day 10 post-infection; n=5-15 mice per group). Flow cytometry results are presented from one experiment (n=5 mice) that was representative of three independent studies. Results were analyzed by One-way ANOVA with Tukey's multiple comparison test (*, p<0.05; **, p<0.01).

To examine this further, biofilm titers and leukocyte infiltrates were quantified in animals receiving 3D bioprinted antibiotic or empty scaffolds at day 7 post-infection, whereupon assessments were performed 3 or 7 days later (corresponding to days 10 and 14 after infection, respectively). While the 3D antibiotic scaffold reduced S. aureus burden by 2-3 log in the galea and brain (FIG. 5A), residual infection was still evident. To augment the bactericidal activity of the 3D antibiotic scaffold, viable macrophages were also incorporated based on their potent antimicrobial activity. The addition of macrophages further reduced S. aureus titers compared to the 3D antibiotic scaffold alone, which was most pronounced in the brain at day 3 after placement (FIG. 5A). The beneficial effect of macrophage addition was transient, in that no additional decrease in titers was observed 7 days after treatment. This is likely explained by the limited half-life of macrophages when exposed to the large number of bacteria contained in the biofilm that produce lytic toxins (Scherr, et al. (2015) mBio 6(4):e01021-15). The combined action of antibiotics and macrophages was required for maximal bacterial clearance, since scaffolds containing macrophages only had little impact on biofilm burdens (FIG. 5A).

Figure 5B:
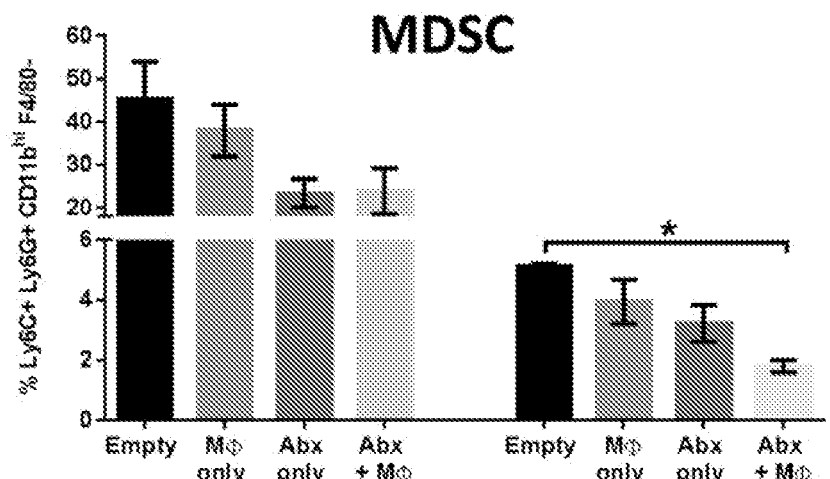
Figure 5C:
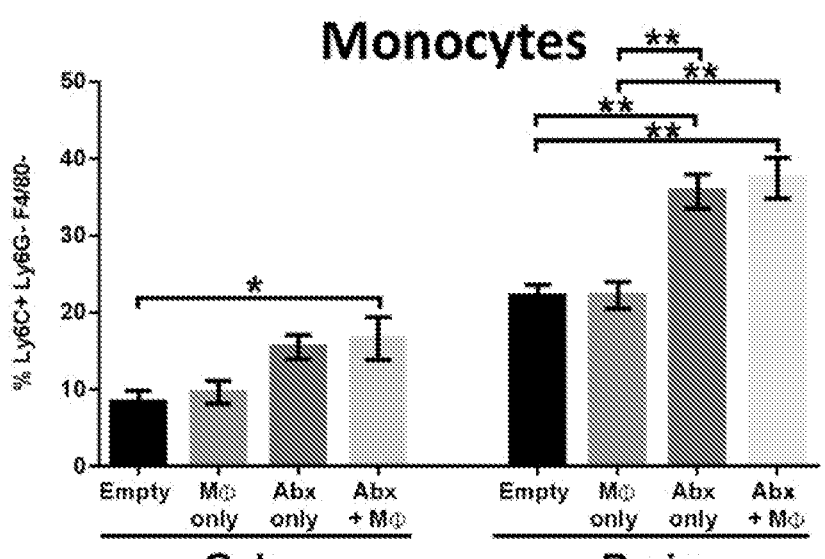

The 3D bioprinted scaffolds also influenced leukocyte recruitment into the galea and brain, as revealed by flow cytometry (FIGS. 5B and C). For this study, two leukocyte populations were studied that are prominent during biofilm-associated infection, namely MDSCs and monocytes (Heim et al. (2018) Infect. Immun., 86(12): e00684-18). MDSCs are immature myeloid cells that inhibit monocyte proinflammatory activity during S. aureus biofilm infection and contribute, in part, to infection persistence (Heim, et al. (2015) J. Leukoc. Biol., 98(6):1003-1013; Heim, et al. (2015) J. Immunol., 194(8):3861-3872; Heim, et al. (2014) J. Immunol., 192(8):3778-3792). In situations where MDSC recruitment is reduced this typically corresponds with an increase in effector cell recruitment (i.e., monocytes) and reduced biofilm burdens (Heim, et al. (2015) J. Leukoc. Biol., 98(6):1003-1013; Heim, et al. (2015) J. Immunol., 194(8): 3861-3872). MDSCs are the most abundant leukocyte population in the galea (FIG. 5B), which represents the region with highest bacterial titers (FIG. 5A). In contrast, MDSC infiltrates are less numerous in the brain (FIG. 5B). 3D antibiotic scaffolds decreased MDSC influx in the galea by approximately 50% compared to empty scaffolds (FIG. 5B), which coincided with increased monocyte recruitment (FIG. 5C). Similar trends with the 3D antibiotic scaffold were observed with MDSC and monocyte recruitment in the brain (FIGS. 5B and 5C). Macrophage incorporation into the Abx scaffold led to significant changes in leukocyte recruitment in the galea and brain compared to empty scaffolds (FIGS. 5B and 5C) and correlated with a reduction in bacterial burdens (FIG. 5A).

Figure 6A:
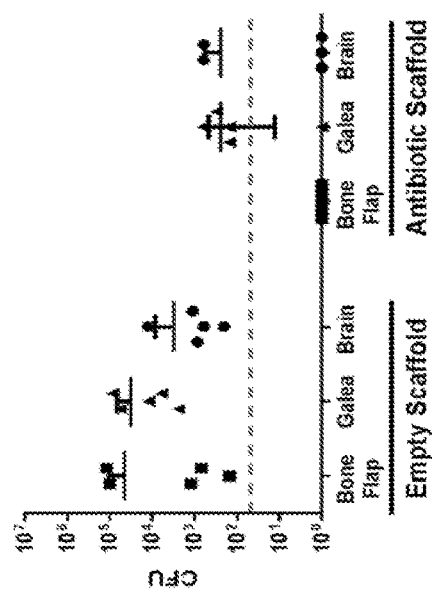
FIGS. 6A-6B show the efficacy of 3D bioprinted antibiotic scaffolds to prevent *S. aureus* craniotomy-associated infection.
Figure 6B:
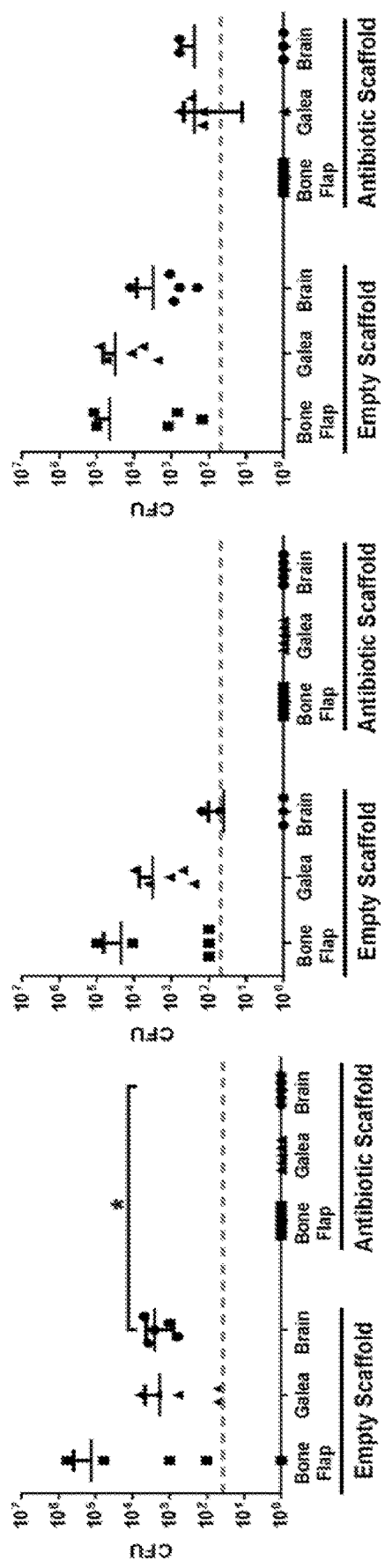

Prevention of Craniotomy-Associated Infection with 3D Bioprinted Antibiotic Scaffolds A prophylactic approach was then evaluated to determine whether 3D bioprinted scaffolds could protect against infectious complications following craniotomy. A craniotomy was performed and a 3D scaffold was placed directly above the sterile bone flap upon reinsertion in the skull. Mice were challenged with various doses of live S. aureus ($10^5$ to $10^7$ CFU) 1 day later by injecting bacteria subcutaneously along the suture site (FIG. 6A). Various inocula were tested to determine the maximal challenge dose that the 3D bioprinted antibiotic scaffold could eradicate to produce a sterile site and facilitate wound healing and recovery. The 3D antibiotic scaffolds were effective at preventing infection in response to challenge with $10^5$ and $10^6$ S. aureus and bacterial burdens were near the lower limit of detection with the $10^7$ inoculum (FIG. 6B).

Figure 7:
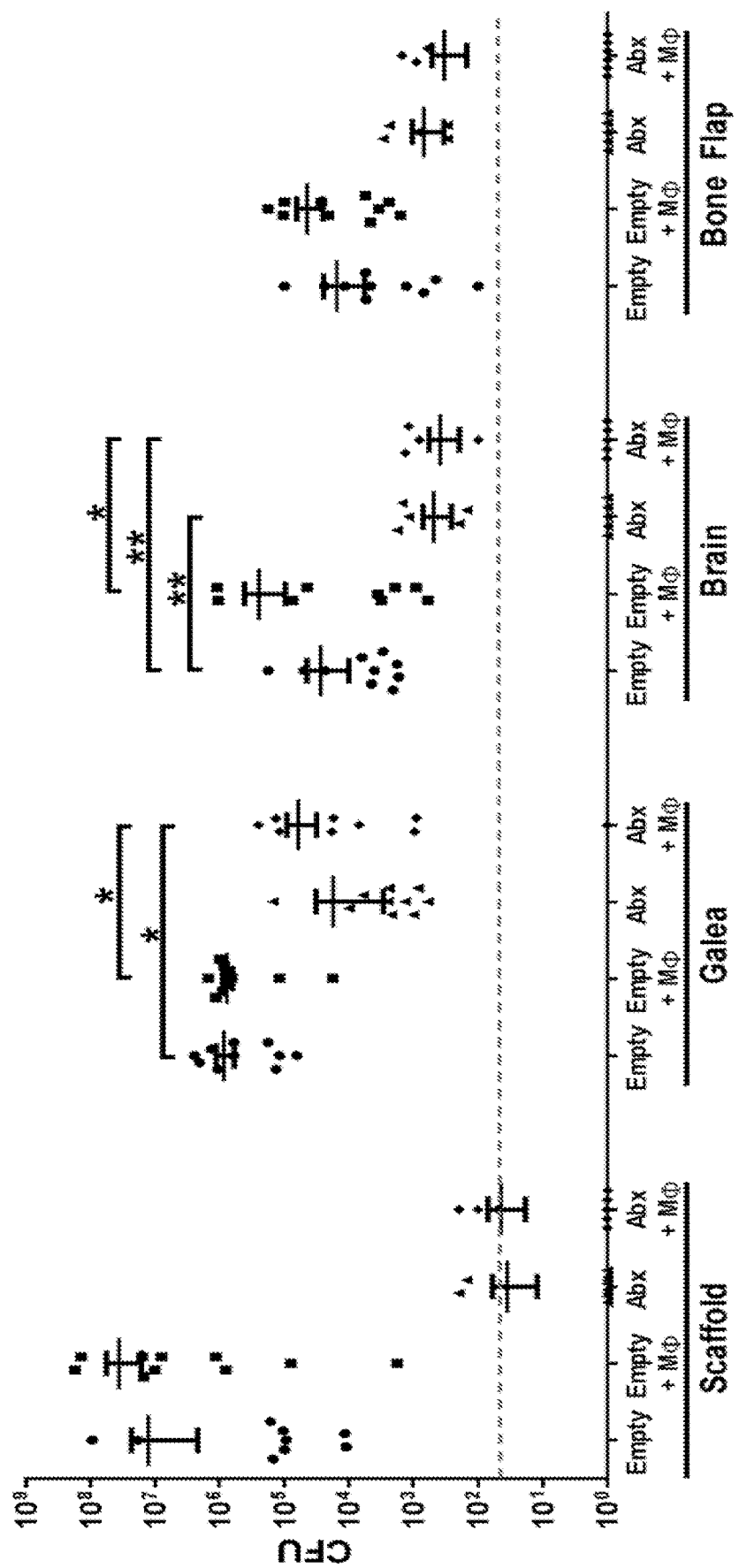
FIG. 7 shows the antibiotic efficacy in a prevention paradigm. 3D bioprinted scaffolds containing antibiotics only (Abx; daptomycin+rifampin), macrophages (MΦs) only, antibiotics+macrophages, or empty scaffolds were placed at the time of craniotomy, whereupon mice (n=8-12 per group) where challenged 1 day later with $10^8$ CFU live S. aureus at the surgical site. Bacterial burdens were determined 7 days later. Results were analyzed by One-way ANOVA with Tukey's multiple comparison test (*, p <0.05; **, p<0.01).

To evaluate whether macrophages would enhance the efficacy of 3D antibiotic scaffolds, a challenge dose of $10^8$ CFU was used to ensure that sufficient bacteria would remain to detect a potential effect of macrophage addition. Unlike the treatment paradigm, the incorporation of macrophages into the 3D scaffold did not greatly potentiate bacterial clearance compared to antibiotics alone (FIG. 7). Nevertheless, the 3D antibiotic scaffold reduced S. aureus titers compared to empty scaffolds and demonstrated excellent efficacy at doses that well exceed what would be encountered during a native infection in patients.

Figure 8A:
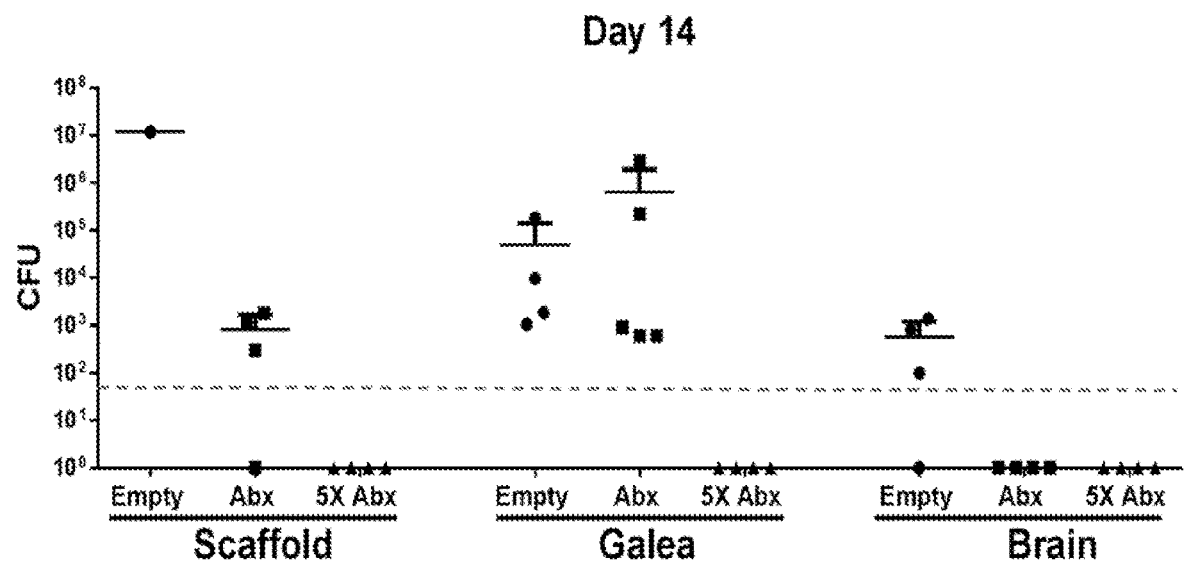
FIGS. 8A-8B show the assessment of the longevity of 3D printed antibiotic scaffolds to treat S. aureus craniotomy infection. 3D bioprinted scaffolds that were empty, containing 20 µg/ml antibiotics (Abx; daptomycin+rifampin), or 5× higher antibiotic concentrations (5×) were placed at day 7 after S. aureus craniotomy infection (n=3-5 mice/group), whereupon bacterial burdens were determined at 14 days (i.e., day 21 post-infection) (FIG. 8A) or 28 days (i.e., day 35 post-infection) (FIG. 8B) following scaffold insertion. Results were analyzed by One-way ANOVA with Tukey's multiple comparison test (*, p<0.05).
Figure 8B:
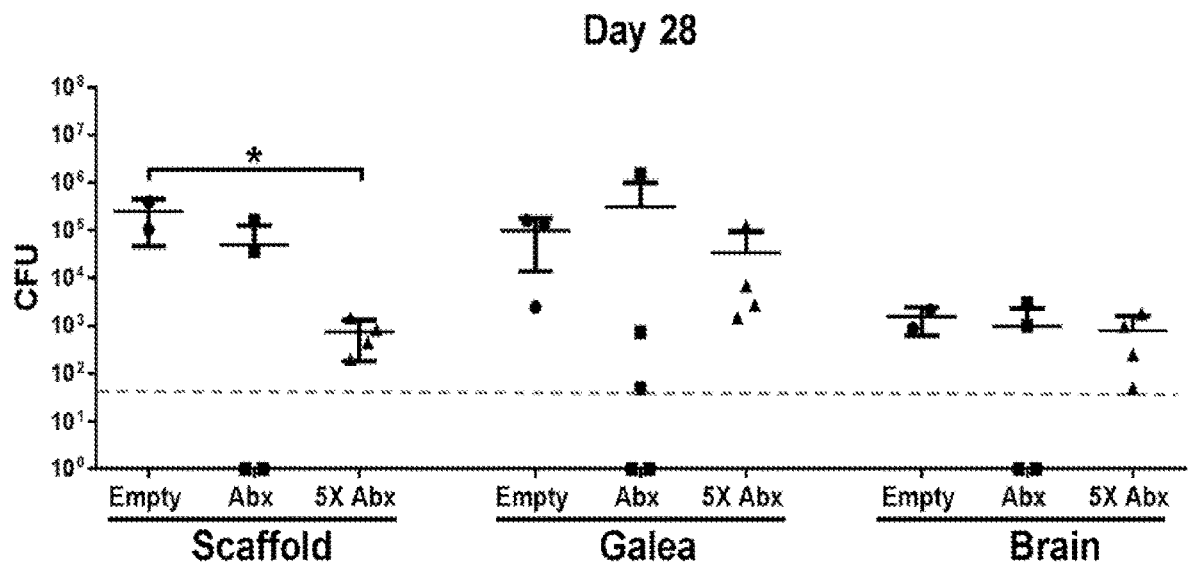

Long-Term Effectiveness of Local 3D Antibiotic Scaffolds and Combination with Systemic Antibiotic Therapy In terms of translational potential, it was important to determine whether the 3D antibiotic scaffold sterilized the infection site or whether bacterial outgrowth would resume after the antibiotic depot had become exhausted (estimated at occur at day 14 based on in vitro studies; FIG. 2C). Macrophages were not examined in these experiments, since they only exhibited beneficial effects at acute time points (i.e. 3 days; FIG. 5). Using the standard antibiotic dose (~16 μg rifampin/mg scaffold and ~18 μg daptomycin/mg scaffold), bacterial burdens began to remerge at day 14 on the scaffold and in the galea, which were further increased at day 28 (FIG. 8). To determine whether outgrowth could be prevented by increasing the antibiotic dose, these experiments were repeated with 3D antibiotic scaffolds that contained 5-fold more antibiotic cocktail. This formulary completely prevented S. aureus recurrence at day 14 following scaffold placement, but by day 28 some bacterial outgrowth was again evident (FIG. 8).

Figures 9A, 9B, 9C:
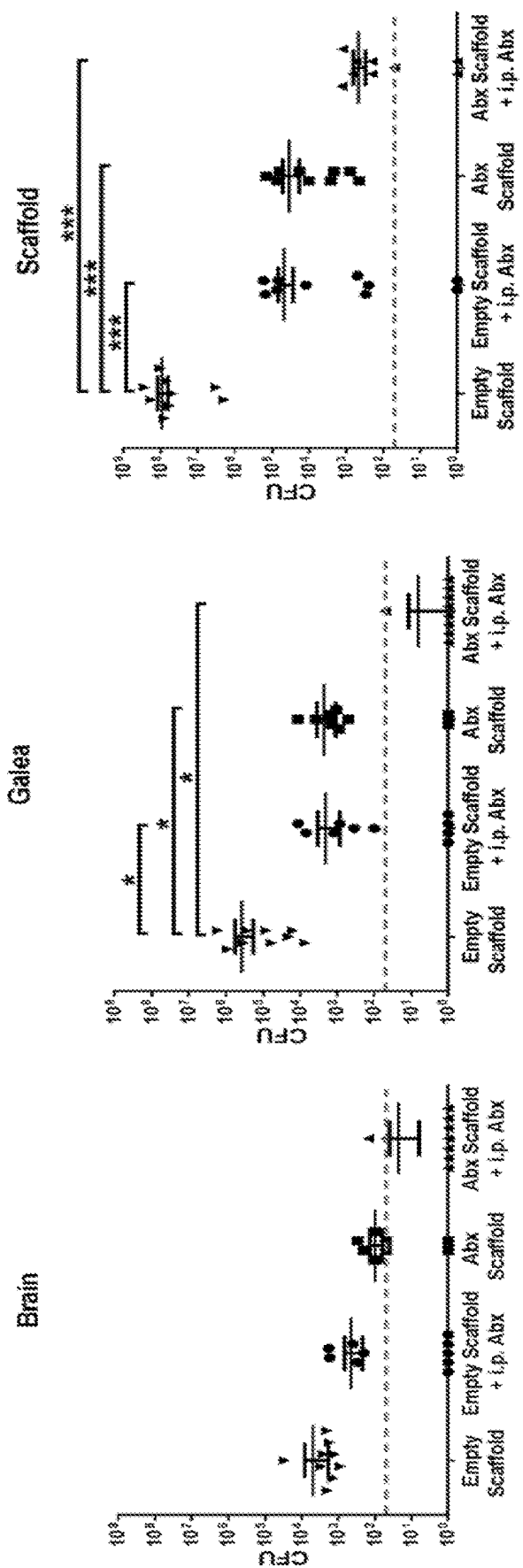
FIGS. 9A-9C show that 3D antibiotic scaffolds synergize with systemic antibiotics to clear established S. aureus craniotomy-associated infection. 3D bioprinted scaffolds that were empty or containing antibiotics only (Abx; daptomycin+rifampin) were placed at day 7 after S. aureus craniotomy infection (n=10 mice/group), whereupon mice received daily i.p. injections of daptomycin and rifampin until sacrifice 7 days later (i.e., day 14 post-infection) and bacterial burdens in the brain (FIG. 9A), galea (FIG. 9B), and scaffold (FIG. 9C) were quantified. Results were analyzed by One-way ANOVA with Tukey's multiple comparison test (*, p<0.05; ***, p<0.001).

Although systemic antibiotics had a limited effect on craniotomy-associated burdens (FIG. 1B), from a clinical perspective, patients with these infections receive systemic antibiotics as a standard-of-care. Therefore, it was assessed whether the combination of systemic antibiotics and the 3D antibiotic scaffold would exert an additive effect. In the earlier studies (FIGS. 6 and 8), higher bacterial inoculums ($10^8$ CFU) were used to prevent complete clearance of the infection, such that effects of macrophages could be assessed. For these experiments, the bacterial inoculum was reduced to $5 \times 10^5$ CFU to recapitulate the lower inoculum that likely occurs in human craniotomy-associated infection. 3D antibiotic scaffolds were placed at day 7 following craniotomy infection coincident with the initiation of daily antibiotic treatment (daptomycin/rifampin) for a period of 7 days. This approach was effective at reducing bacterial burdens near or below the level of detection, indicating progression towards an effective clinical outcome (FIG. 9).

Biofilm infections are difficult to treat because a subpopulation of bacteria are metabolically dormant (Wood, et al. (2013) Appl. Environ. Microbiol., 79(23):7116-7121; Lewis, et al. (2007) Nat. Rev. Microbiol., 5(1):48-56). In terms of craniotomy-associated infection this is magnified by the protracted period required for therapeutic antibiotic concentrations to be achieved in the brain due to BBB exclusion (Nau, et al. (2010) Clin. Microbiol. Rev., 23(4): 858-883). This study examined the efficacy of a device designed to demonstrate reducing bacterial burdens following craniotomy-associated infection. A localized delivery approach with a 3D bioprinted bone scaffold facilitates more rapid therapeutic benefit based on proximity to the infection site coupled with consistent slow-release to ensure steady therapeutic concentrations. The results support these findings, where systemic antibiotics alone were less effective at clearing craniotomy-associated infection, but local delivery with 3D printed antibiotic scaffolds reduced S. aureus burdens. Furthermore, the combination of the 3D antibiotic scaffold and systemic antibiotic delivery demonstrated superior efficacy at clearing infection. This is likely because the 3D scaffold reduced biofilm burdens, which would be expected to alter biofilm architecture, resulting in the transition to a planktonic growth state that is amenable to antibiotic action.

It was also examined whether an immune-based approach incorporated into the 3D scaffold would synergize with antibiotics to promote biofilm clearance. This was realized by bioprinting viable macrophages into the antibiotic scaffold. Macrophages are professional phagocytes and were envisioned to promote biofilm dispersal, which would transform dormant biofilm-associated bacteria into a metabolically active planktonic state, sensitizing them to antibiotic clearance (Lewis, K. (2007) Nat. Rev. Microbiol., 5(1):48-56). Interestingly, a beneficial effect of macrophages to potentiate bacterial clearance was most evident in the brain, whereas a trend towards reduced titers was also detected in the galea. This might be explained by the lower bacterial burdens in the brain compared to galea, which were more amenable to immune-mediated clearance.

With regard to the mechanism, macrophages may migrate out of the porous gel scaffold into the brain parenchyma to exert direct antibacterial activity. Alternatively, activated macrophages may secrete cytokines/chemokines that augment the antimicrobial activity of other glia/leukocytes associated with the infection. However, neither of these possibilities are mutually exclusive and both could be operative. Nevertheless, the results demonstrate that the beneficial effects of macrophages are short-lived, since their impact was only observed 3 days following 3D scaffold treatment, which was lost at day 7. Macrophages were effective in facilitating S. aureus clearance from established biofilms (i.e., treatment initiated at day 7 post-infection), whereas they did not greatly improve bacterial killing in the prevention paradigm. One possibility to explain this observation is that a robust milieu of cytokines and growth factors is present in an established biofilm (Cheatle, et al. (2013) Am. J. Pathol., 183(2):450-458; Heim, et al. (2015) J. Leukoc. Biol., 98(6):1003-1013; Heim, et al. (2015) J. Immunol., 194(8):3861-3872), which may deliver pro-survival signals to macrophages within the 3D scaffold and promote their antibacterial activity. In contrast, when 3D antibiotic/macrophage scaffolds are placed at the time of surgery and infection is delayed until the following day, macrophages are not bathed in a growth factor-enriched environment and conceivably to do not receive signals to promote their viability or prime their pro-inflammatory activity in response to a subsequent bacterial challenge. As such, the inclusion of cytokines with the macrophages may increase their efficacy.

The 3D scaffolds may be modified to contain matrix materials that are biodegradable, are more inert, and/or possess inherent antimicrobial properties. The 3D scaffolds may also be engineered to contain immune-modifying molecules to augment the pro-inflammatory properties of biofilm-associated leukocytes and/or glia (e.g., rather than incorporating live immune cells). The 3D scaffolds may also be used with an immune-mediated strategy to promote biofilm dispersal in order to potentiate efficacy.

The 3D antibiotic scaffold prevented infection establishment with a challenge dose of $10^5$ S. aureus, which is expected to exceed the number of organisms that would seed a site during native infection in humans. These studies demonstrate the ability of a 3D bioprinting approach to mitigate bacterial burdens when scaffolds are placed at the site of craniotomy infection, optionally in combination with systemic antibiotics.

EXAMPLE 2

New strategies for 3D printing alginate (Alg)-based materials onto the antibiotic scaffolds are provided.

First, Alg was modified with 11-azido-3,6,9-trioxa undecan-1-amine to generate Alg-PEG-azide. Alg (FMC Biopolymer; 200 mg) was dissolved in 40 mL of 2-(N-morpholino)ethanesulfonic acid (MES) buffer (0.1 M, pH 5.5) and mixed thoroughly with 100 µL of 11-azido-3,6,9-trioxaundecan-1-amine (BroadPharm) for 1 hour at room temperature. Then 100 mg of N-(3-dimethylaminopropyl)-N'-ethylcarbodiimide hydrochloride (EDC.HCl) and 60 mg of N-hydroxysuccinimide (NHS) was added. The whole mixture was adjusted to pH 5.5 and stirred for another 48 hours. After that, the mixture was transferred into a dialysis bag (6-8 kDa) and dialyzed against water for 3 days with the water change every 12 hours. The final product was lyophilized and stored at −20° C. before use.

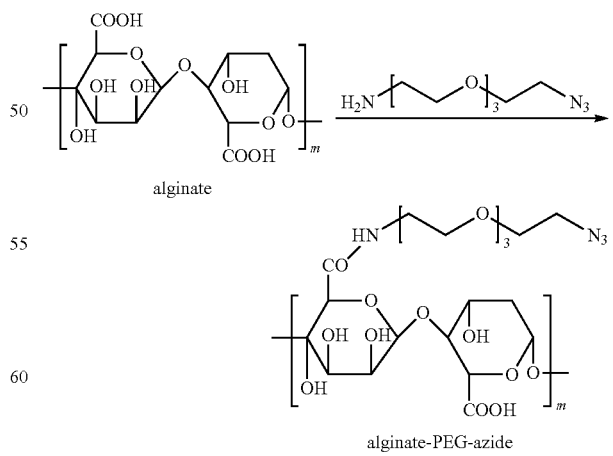

Additionally, daptomycin can be modified with dibenzocyclooctyne-N-hydroxysuccinimidyl ester (DBCO-NHS ester) to generate DBCO-daptomycin.

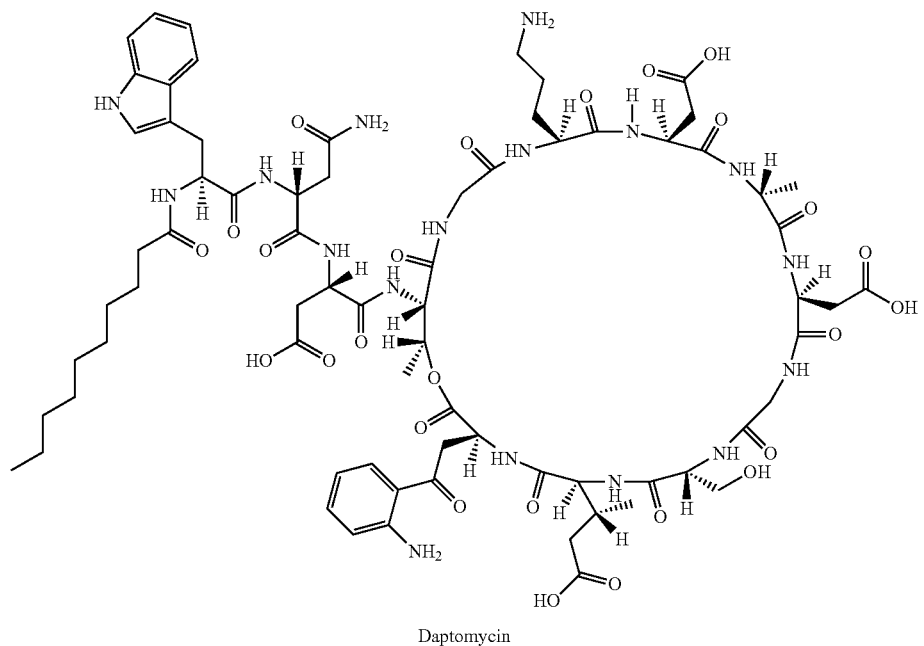
Daptomycin
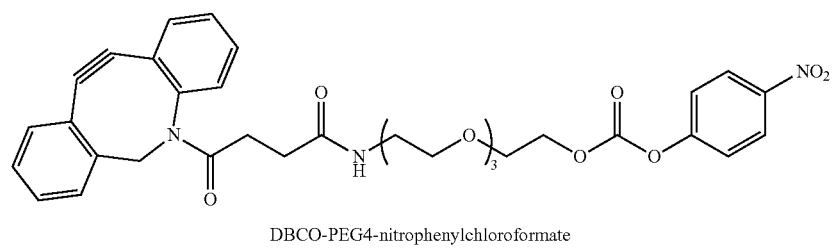
DBCO-PEG4-nitrophenylchloroformate
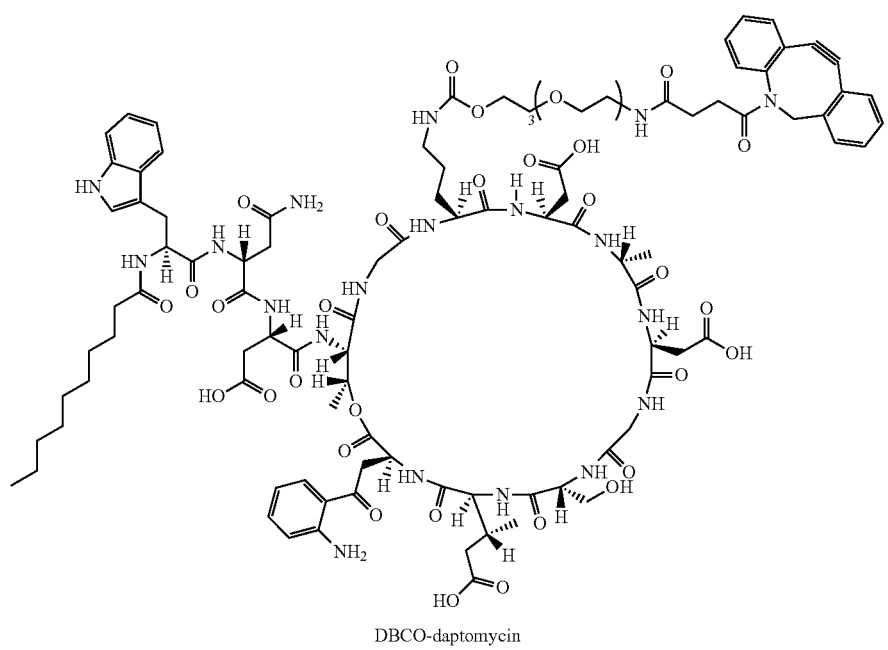
DBCO-daptomycin The synthesized Alg-PEG-azide can undergo a click reaction with DBCO-daptomycin and form Alg-PEG-daptomycin.

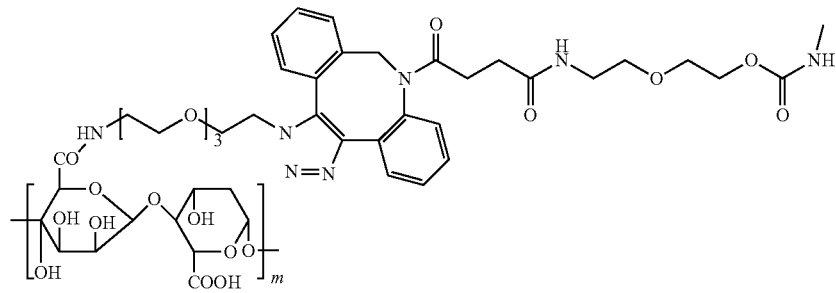

Alg-PEG-daptomycin

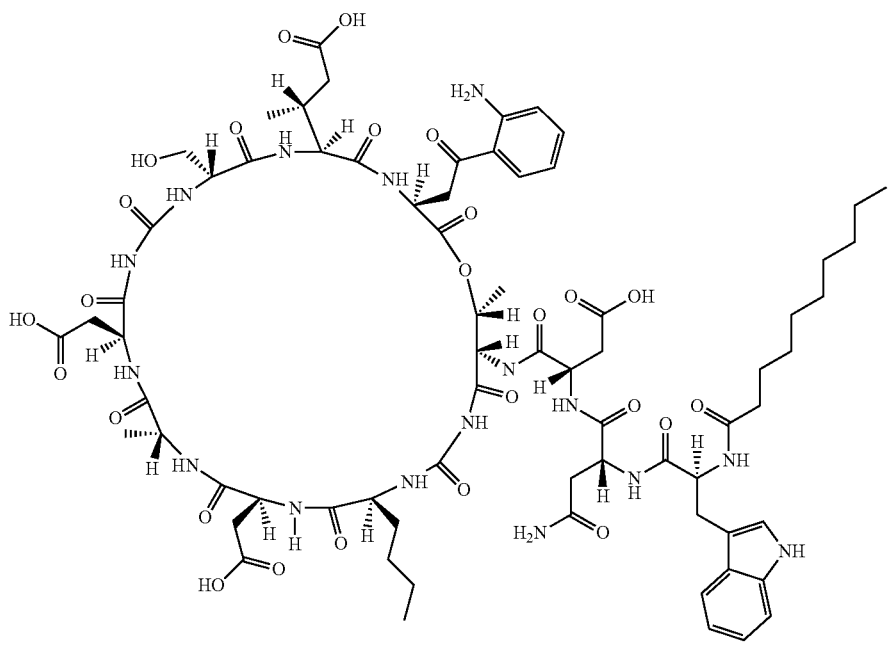

The Alg-PEG-daptomycin can be directly printed onto antibiotic scaffolds to potentiate the sustained release of daptomycin to clear the bacteria (FIG. 10A). The Alg-PEG-azide can also be printed onto antibiotic scaffolds with DBCO-daptomycin administrated systematically (FIG. 10B). The DBCO-daptomycin will click react with Alg-PEG-azide when it circulates at the cranial region to exert antibacterial activity. The click reaction approach will refill the antibiotic (daptomycin) to the scaffold after the 3D printed antibiotic has completely released, which will effectively decrease the frequency of systemic antibiotic administration.

In order to confirm the click reaction, a dye (sulfo-Cy3-DBCO) was used to react with Alg-PEG-azide. Briefly, an in vitro reaction was conducted by incubating 25 μg/mL of DBCO-daptomycin/sulfo-Cy3-DBCO with the alginate-$N_3$ hydrogel in PBS overnight. The alginate-$N_3$ hydrogel was prepared by first dissolving 4% (w/v) previously synthesized alginate-$N_3$ in PBS and then mixed with 0.5% (w/v) $CaCl_2$ solution at a pre-determined ratio (7/3 v/v). Every 100 μL of the mixture was then extruded into an 8 mm mold and then immersed into 2.5% (w/v) $CaCl_2$ solution for 2 minutes. After an overnight incubation, the DBCO-daptomycin/sulfo-Cy3-DBCO conjugated alginate-$N_3$ hydrogel was collected for further testing.

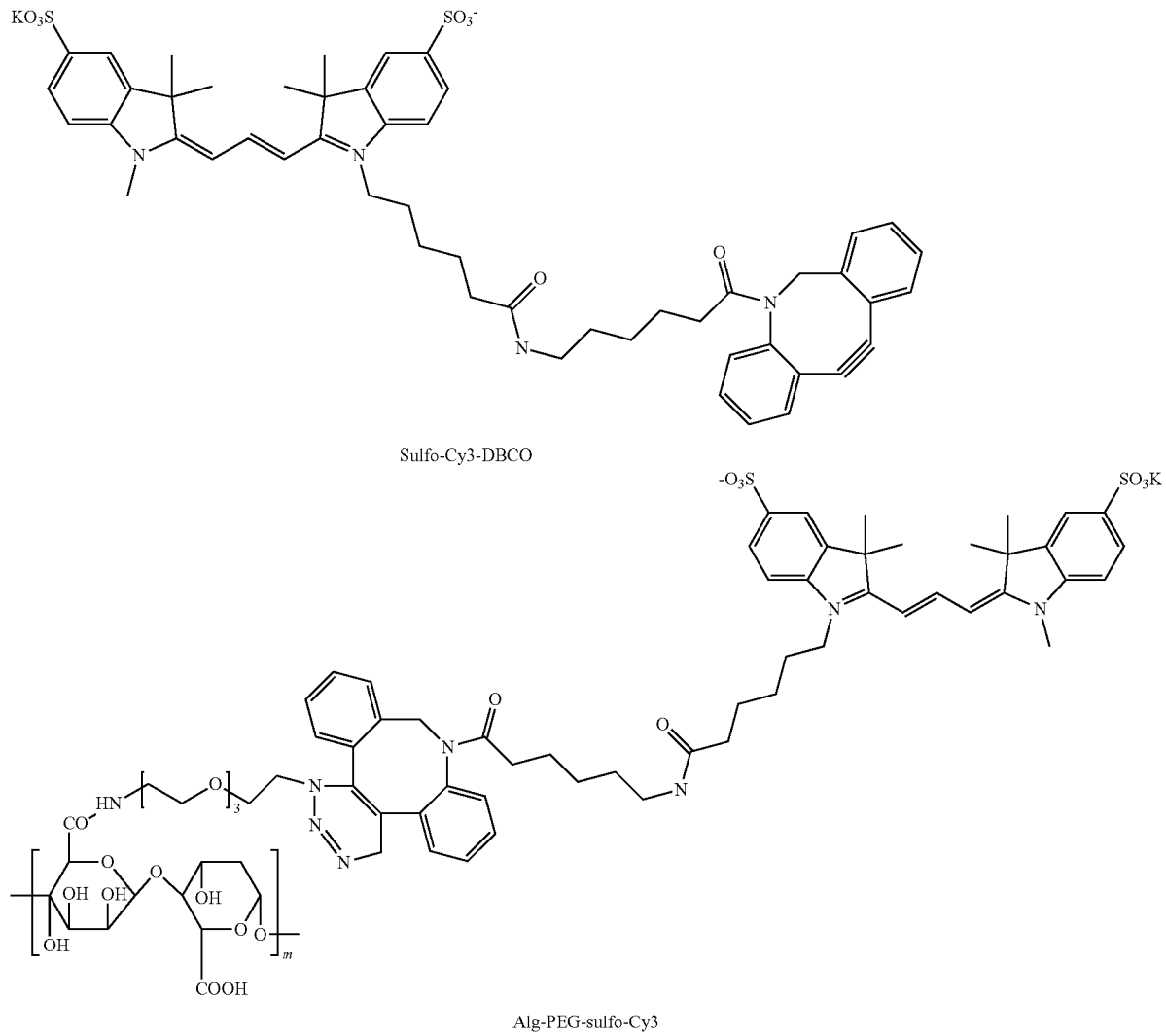

Sulfo-Cy3-DBCO

Alg-PEG-sulfo-Cy3

Figure 11A:
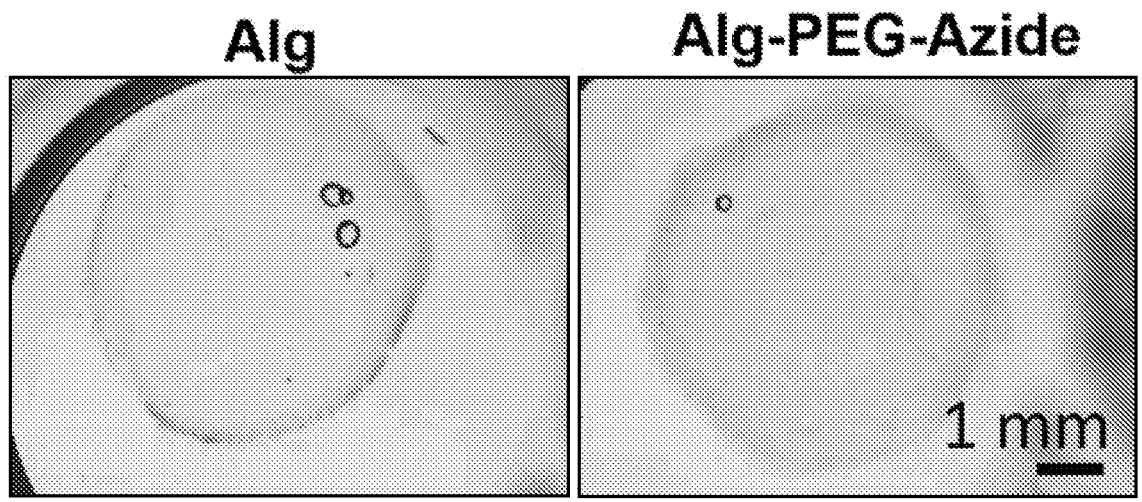
FIG. 11A provides images of alginate and alginate-PEG-Azide discs mixed with Sulfo-Cy3-DBCO overnight and then washed with PBS.
Figure 11B:
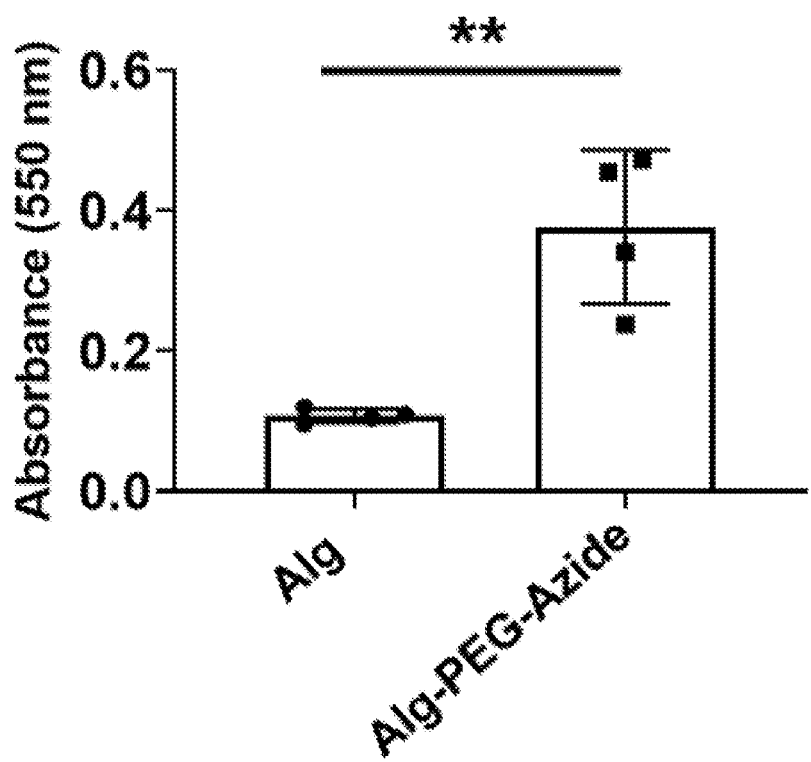
FIG. 11B provides the absorbance of the discs after the click reaction as measured by microplate reader.

In FIG. 11A, sulfo-Cy3-DBCO successfully reacted with the Alg-PEG-azide based gel, depicted by a pink color, whereas no reaction or color change was detected with Alg. A quantitative absorbance test also confirmed that significantly more sulfo-Cy3-DBCO was attached to Alg-PEG-azide (FIG. 11B).

Figure 12B:
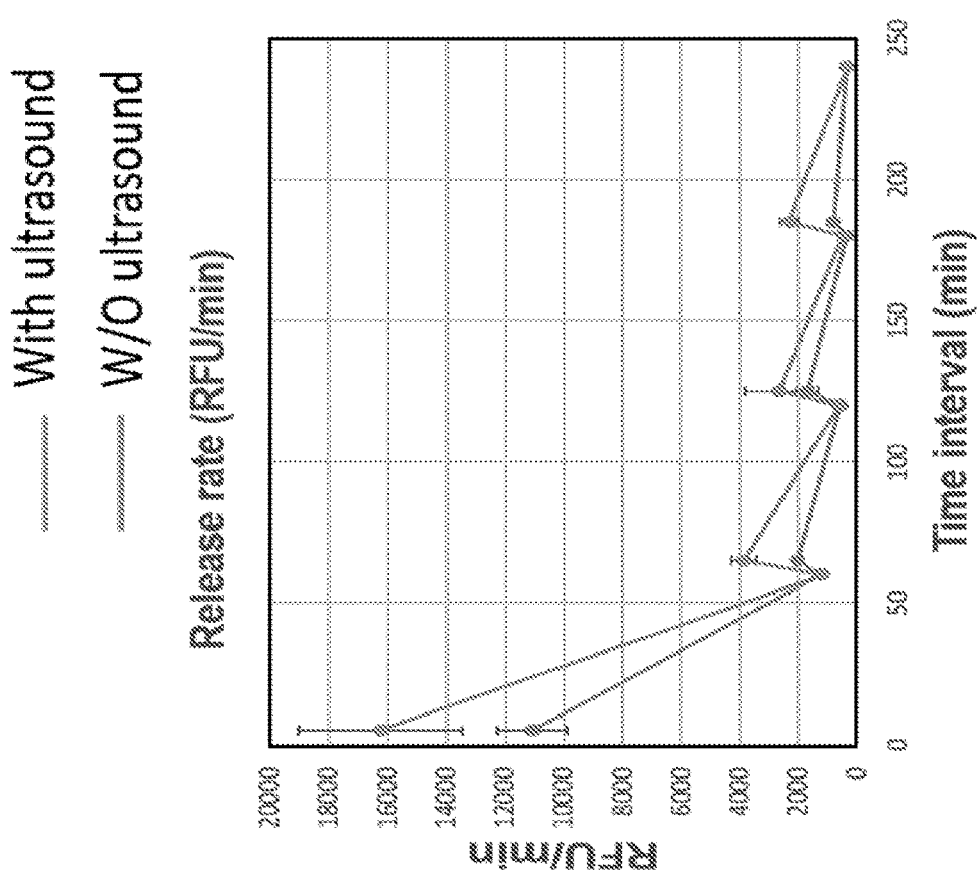
FIG. 12B provides a graph of the release rate.
Figure 12A:
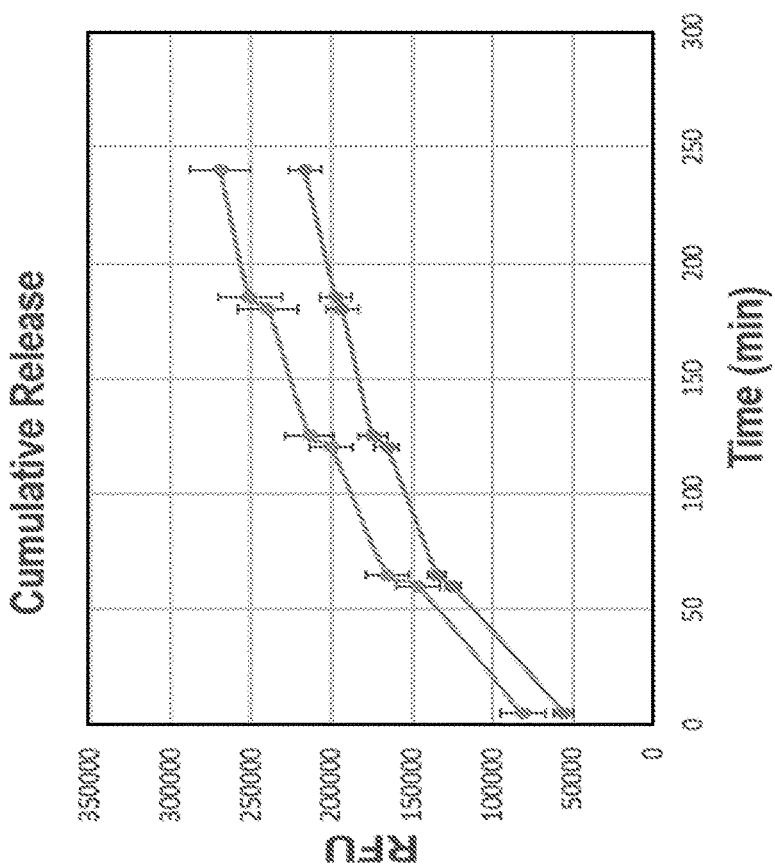
FIG. 12A provides a graph of the cumulative release of FITC-BSA. Ultrasound was applied for 5 minutes every hour for 4 hours.

In addition to the above, an ultrasound triggered delivery system to mitigate bacterial or biofilm infection can be used. Microspheres (MS) loaded with antibiotics or antimicrobial peptides can be fabricated and incorporated into Alg. Then, Alg-MS can be 3D printed onto the 3D antibiotic scaffolds. Applying ultrasound will disrupt the ionically cross-linked Alg hydrogels and induce the release of loaded drugs (FIG. 10C). The rationale for this approach is based on the finding that bacteria began to reemerge 2 weeks following treatment with 3D antibiotic scaffolds in a mouse model of craniotomy-associated infection. The incorporation of loaded MS will allow for the delivery of a second wave of antimicrobial activity after the release of antibiotics from the 3D scaffold, to mitigate the outgrowth of residual bacteria. This is a tractable clinical approach based on the non-invasive nature and safety record of ultrasound. A proof-of-concept experiment was conducted by loading FITC-BSA into Alg and applying ultrasound. FITC-BSA was encapsulated into poly(lactic-co-glycolic acid) (PLGA) microspheres (MS). Then FITC-BSA-PLGA MS were loaded into Alg solution and then fabricated into Alg discs with FITC-BSA-PLGA MS. The discs were immersed in PBS and then subjected to ultrasound (1 Hz, 5 minutes, continuous mode, 1 W/cm$^2$). Ultrasound was applied for 5 minutes every hour for 4 hours. It was found that significantly more FITC-BSA was released with much higher release speed (FIGS. 12A and 12B).

EXAMPLE 3

As explained above, a mouse model of *S. aureus* craniotomy-associated biofilm infection was used. In this model, a craniotomy is performed and the excised bone flap is incubated with *S. aureus* for 5 minutes, whereupon the bone is rinsed to remove any non-adherent bacteria and reinserted. This procedure results in *S. aureus* colonization of the bone flap on both surfaces, which ultimately leads to infection persistence in the subcutaneous galea and brain that cannot be cleared with antibiotics, which is the functional definition of a biofilm. The structural characteristics of biofilm from a patient with confirmed *S. aureus* craniotomy-associated infection has been compared to the mouse model and they are indistinguishable (Cheatle, et al. (2013) Am. J. Pathol., 183(2):450-458). Likewise, the MII changes observed during the course of *S. aureus* craniotomy-associated biofilm infection in the mouse closely model human disease (Cheatle, et al. (2013) Am. J. Pathol., 183(2):450-458). Infection persistence in the mouse has been demonstrated out to 9 months, which is reminiscent of craniotomy-associated infection in humans that cannot be cleared with conventional antibiotics alone. The similarities between human craniotomy-associated infection and the mouse model support its use to evaluate the efficacy of the novel 3D bioprinted scaffold that incorporates pro-inflammatory macrophages to promote biofilm dispersal, which, in turn, induces bacterial susceptibility to the sustained release antibiotic formulation in the scaffold.

From a therapeutic perspective, biofilm infections are difficult to eradicate, which was originally thought to result, in part, from the ability of biofilm-associated bacteria to passively escape immune detection (del Pozo, et al. (2007) Clin. Pharmacol. Ther., 82(2):204-209; Davies, D. (2003) Nat. Rev. Drug Discov., 2(2):114-122). However, it has been established that staphylococcal biofilms actively reprogram the host innate immune response to favor bacterial persistence (Thurlow, et al. (2011) J. Immunol., 186(11):6585-6596; Hanke, et al. (2012) PLoS One, 7(8):e42476; Hanke, et al. (2012) Front. Cell. Infect. Microbiol., 2:62; Schommer, et al. (2011) Infect. Immun., 79(6):2267-2276; Spiliopoulou, et al. (2012) FEMS Microbiol Lett., 330(1):56-65; Cerca, et al. (2011) J. Med. Microbiol., 60(Pt 12):1717-1724). For example, *S. aureus* biofilms circumvent Toll-like receptor recognition, which is critical for the clearance of planktonic bacteria (Thurlow, et al. (2011) J. Immunol., 186(11):6585-6596). Endogenous macrophages are not capable of phagocytosing biofilm-associated bacteria and undergo rapid cell death, which has been attributed to both the inability to engulf the thick biofilm structure and bacterial toxins (Thurlow, et al. (2011) J. Immunol., 186(11):6585-6596; Scherr, et al. (2015) mBio, 6(4):e01021-15). In vivo, *S. aureus* biofilms are associated with the accumulation of macrophages that are programmed towards an anti-inflammatory state with impaired bactericidal activity (Thurlow, et al. (2011) J. Immunol., 186(11):6585-6596). In addition to biofilm-derived factors, a pathological role was identified for myeloid-derived suppressor cells (MDSCs) in promoting biofilm persistence during *S. aureus* implant-associated infection by polarizing macrophages to an anti-inflammatory phenotype (Thurlow, et al. (2011) J. Immunol., 186(11):6585-6596; Heim, et al. (2014) J. Immunol., 192(8):3778-3792; Heim, et al. (2015) J. Leukoc. Biol., 98(6):1003-1013; Heim, et al. (2015) J. Immunol., 194(8):3861-3872). MDSCs are a heterogeneous population of immature monocytes and granulocytes that are potent inhibitors of T cell activation (Gabrilovich, D. I. (2017) Cancer Immunol. Res., 5(1):3-8). MDSCs normally reside in the bone marrow prior to their differentiation into mature granulocytes, macrophages, or dendritic cells. However, MDSCs can be recruited into inflamed tissues during pathologic conditions by the actions of growth factors, such as granulocyte colony-stimulating factor (G-CSF), granulocyte-macrophage colony-stimulating factor (GM-CSF), and vascular endothelial growth factor (VEGF), where disturbances in cytokine homeostasis block their differentiation into mature myeloid effector cells, resulting in MDSC expansion (Gabrilovich, D. I. (2017) Cancer Immunol. Res., 5(1):3-8). During sterile inflammation, MDSCs have the potential to differentiate into mature macrophages and neutrophils (PMNs) (Gabrilovich, et al. (2009) Nat. Rev. Immunol., 9(3):162-174). However, in some pathological conditions, such as *S. aureus* biofilm infections (Heim, et al. (2014) J. Immunol., 192(8):3778-3792; Heim, et al. (2015) J. Leukoc. Biol., 98(6):1003-1013; Heim, et al. (2015) J. Immunol., 194(8):3861-3872), MDSCs remain arrested in an immature state, where they negatively influence microbicidal mechanisms through their suppressive actions (Gabrilovich, et al. (2012) Nat. Rev. Immunol., 12(4):253-268).

Figure 13:
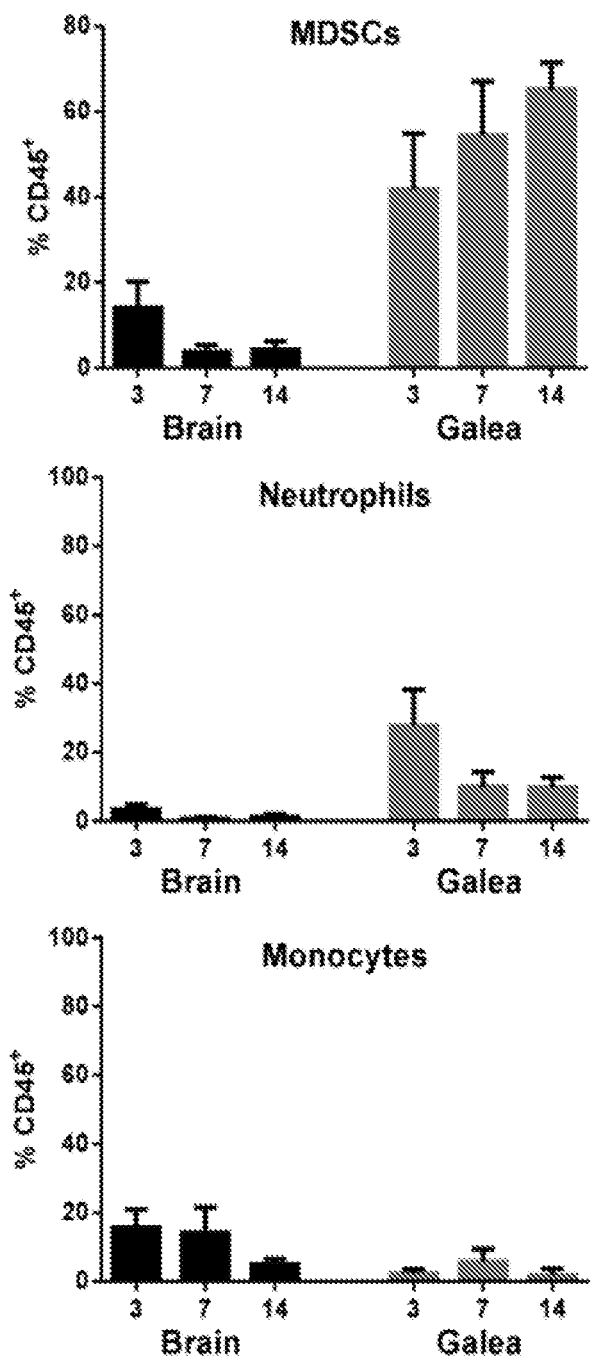
FIG. 13 shows preferential leukocyte recruitment in the galea vs. brain during S. aureus craniotomy-associated infection. Mice were sacrificed at the indicated days after S. aureus craniotomy infection, whereupon immune cell infiltrates were determined by FACS. Results are reported as the percentage of the total CD45% leukocyte population.
Figure 14:
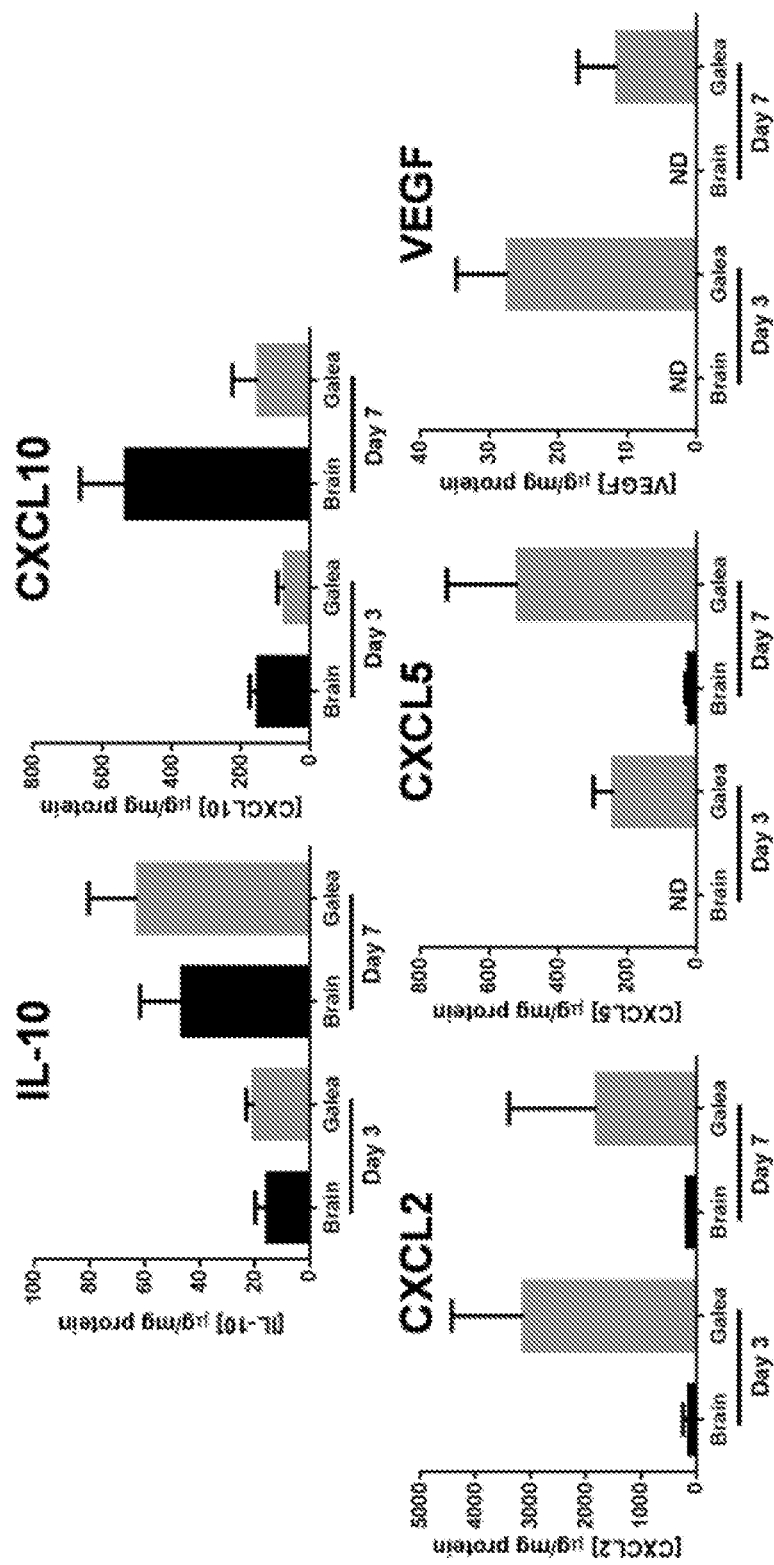
FIG. 14 shows preferential mediator expression in the galea vs. brain during craniotomy infection. Mice were sacrificed at the indicated time points after S. aureus infection, whereupon inflammatory mediator production was quantified using Milliplex® multi-analyte assays. Results are reported as the [mediator]/mg protein to correct for differences in tissue sampling size (ND=not detected).

Unlike biofilm infections in the periphery, numerous inflammatory responses have been identified that are preferentially biased to the galea vs. brain during *S. aureus* craniotomy-associated biofilm infection. For example, PMN infiltrates are limited to the galea, whereas monocytes (MO) (FIG. 13) are most prominent in the brain, where they differentiate into macrophages. MDSCs are present in both compartments, but are most abundant in the galea, which agrees with increased macrophage inflammatory protein-2 (CXCL2) and regulated upon activation T cell expressed and secreted (RANTES; CXCL5) expression in the galea, since both chemokines have been reported to induce MDSC and PMN recruitment (FIG. 14). Therefore, although macrophages are recruited to biofilm infections, they receive signals from both the biofilm and infiltrating MDSCs to downregulate their bactericidal activity, which contributes to biofilm persistence. The 3D printed scaffolds of the instant invention allow for the reversal of the anti-inflammatory properties of biofilm-associated macrophages to promote bacterial dispersal from the biofilm, whereupon bacteria would then be susceptible to antibiotic-mediated killing that synergizes with macrophage microbicidal activity.

The introduction of pro-inflammatory macrophages into sites of *S. aureus* biofilm infection is capable of partially reducing bacterial burdens and restored the biofilm milieu to a pro-inflammatory state, which likely facilitated bacterial clearance (Hanke, et al. (2013) J. Immunol., 190(5):2159-2168). The ability of pro-inflammatory macrophages was exploited to induce biofilm dispersal together with sustained antibiotic release in the 3D bioprinted scaffold. The inclusion of pro-inflammatory macrophages significantly reduces biofilm burdens almost below the level of detection (FIG. 15 (see also FIG. 7)).

Figure 15:
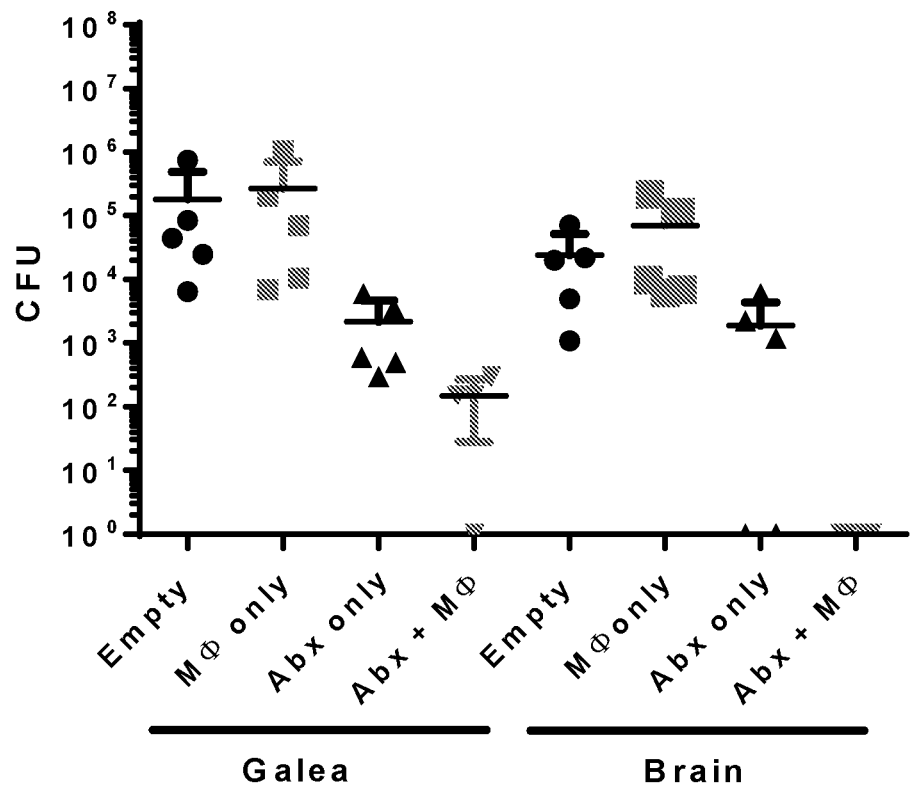
FIG. 15 shows the synergistic action of 3D bioprinted scaffolds containing pro-inflammatory macrophages and antibiotic cocktail to treat established MRSA craniotomy-associated infection. 3D bioprinted scaffolds containing pro-inflammatory macrophages, antibiotics (daptomycin/rifampin), or both were placed at day 7 following S. aureus craniotomy infection, whereupon bacterial burdens were determined three days later (i.e. day 10 post-infection). Empty scaffolds were included as a control to assess the therapeutic efficacy of the various 3D bioprinted scaffolds.

It is well-established that macrophages can be polarized towards a pro- or anti-inflammatory state depending on the local milieu (Gordon, et al. (2010) Immunity 32(5):593-604). For example, pro-inflammatory signals such as IFN-γ and *S. aureus*-derived peptidoglycan (PGN) induce pro-inflammatory macrophages that exert potent anti-bacterial activity (Hanke, et al. (2013) J. Immunol., 190(5):2159-2168). In contrast, *S. aureus* biofilms skew macrophages away from a pro-inflammatory microbicidal phenotype to favor anti-inflammatory, pro-fibrotic pathways (Thurlow, et al. (2011) J. Immunol., 186(11):6585-6596; Hanke, et al. (2012) PLoS One, 7(8):e42476; Hanke, et al. (2013) J. Immunol., 190(5):2159-2168). This is compounded by the finding that resident tissue macrophages do not invade the biofilm to physically contact the bacteria and display impaired phagocytosis (Thurlow, et al. (2011) J. Immunol., 186(11):6585-6596; Scherr, et al. (2015) mBio 6(4):e01021-15). These factors likely account for biofilm persistence and the robust fibrotic response that often encases these infections. The introduction of exogenous macrophages facilitates biofilm clearance and the current studies demonstrate the efficacy of pro-inflammatory skewed macrophages to synergize with a 3D bioprinted antibiotic scaffold. Scaffolds containing both antibiotics and pro-inflammatory macrophages synergize to promote *S. aureus* craniotomy-associated biofilm clearance compared to either antibiotics or macrophages alone (FIG. 15). Importantly, no viable bacteria were associated with the 3D antibiotic scaffold, indicating that the scaffold is not acting as a foreign body.

Figures 16A, 16B, 16C:
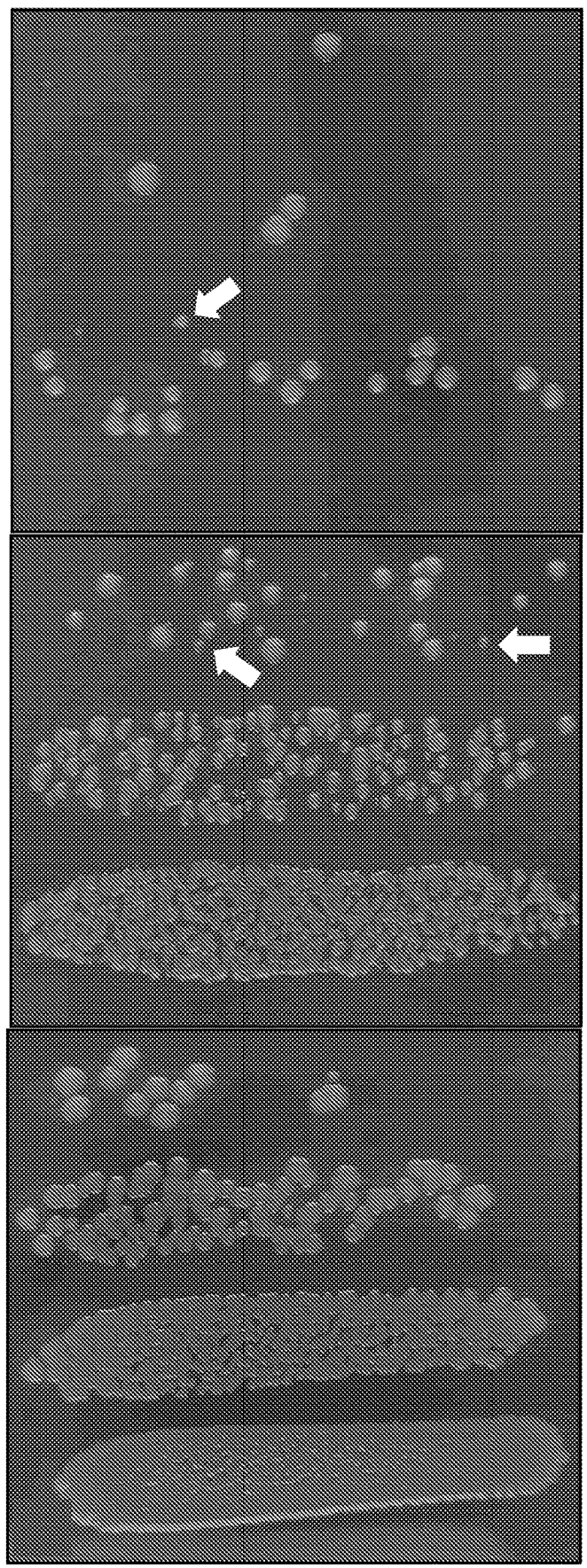
FIGS. 16A-16C provide images of bacteria recovered from the subcutaneous galea of mice receiving 3D scaffolds containing antibiotics alone (FIG. 16B) or antibiotics and pro-inflammatory macrophages (FIG. 16C) at day 3 following S. aureus craniotomy infection. Small colonies (arrows) are identified and loss of staphyloxanthan pigment is seen compared to animals receiving empty scaffolds (FIG. 16A).

Bacterial burdens associated with the scaffold, bone flap, subcutaneous tissue (galea), and underlying brain parenchyma may be quantified by plating on blood agar and trypticase soy agar (TSA) plates to assess the degree of hemolysis and staphyloxanthin pigment production, respectively. These attributes can provide information about how the 3D antibiotic scaffold and macrophages impact S. aureus fitness. For example, hemolysis is induced by a cadre of lytic toxins that also kill immune cells (Spaan, et al. (2017) Nat. Rev. Microbiol., 15(7):435-447; Thammavongsa, et al. (2015) Nat. Rev. Microbiol., 13(9):529-543), and reduced hemolysis following 3D antibiotic scaffold and macrophage treatment would be expected to limit immune cell lysis, effectively providing more effector cells to kill bacteria. The staphyloxanthin pigment of S. aureus is a known antioxidant that facilitates evasion of hydrogen peroxide-mediated killing (Liu, et al. (2005) J. Exp. Med., 202(2):209-215). Therefore, reduced pigment production with the 3D antibiotic and macrophage scaffold would translate into increased susceptibility to phagocyte killing. As seen in FIG. 16, the 3D antibiotic scaffold and pro-inflammatory macrophages inhibited both lysis and staphyloxanthin pigment production. Therefore, the positive impact of reduced toxin and pigment production on promoting leukocyte survival and antibacterial function, respectively, would synergize with antibiotics in the scaffold to promote S. aureus clearance.

Figure 17:
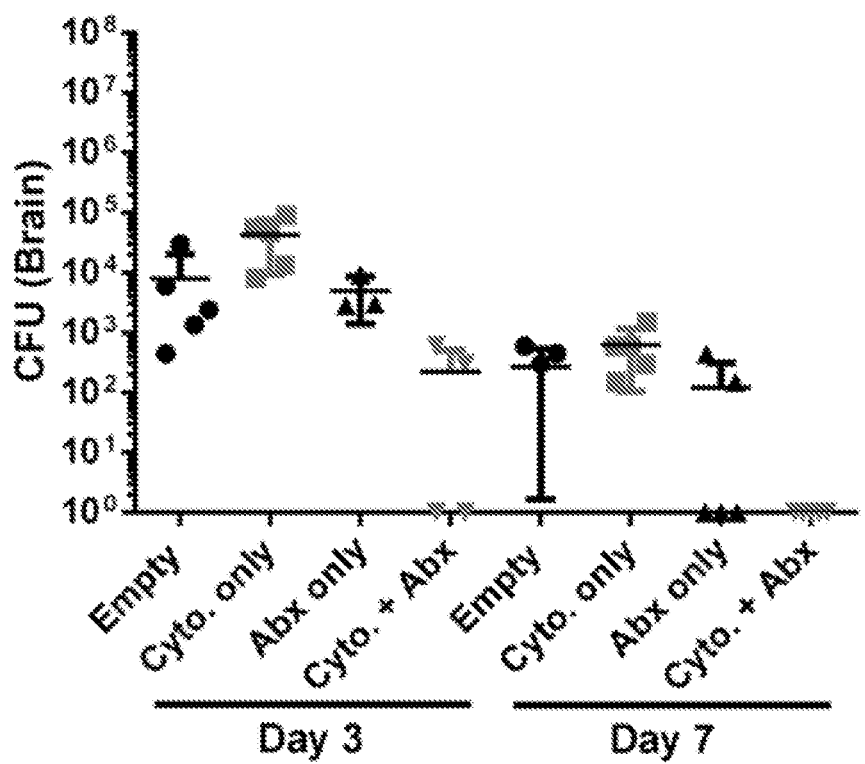
FIG. 17 shows that 3D bioprinted scaffolds containing macrophage-activating cytokines promote MRSA clearance in the brain. 3D bioprinted scaffolds containing macrophage-activating cytokines (Cyto; IFN-γ and M-CSF), antibiotics (Abx; daptomycin/rifampin), or both were placed at day 7 following S. aureus craniotomy infection, whereupon bacterial burdens in the brain were determined 3 and 7 days later (i.e. days 10 and 14 post-infection). Empty scaffolds were included as a control to assess the therapeutic efficacy of the various 3D bioprinted scaffolds.

It was then examined whether incorporating a macrophage-activating cytokine cocktail in the 3D scaffold is capable of reprogramming endogenous biofilm-associated macrophages into a pro-inflammatory microbicidal state to facilitate biofilm clearance. This can be achieved with a combination of M-CSF and IFN-γ, to stimulate macrophage maturation and prime pro-inflammatory activity at the site of biofilm infection, respectively (Adams, et al. (1984) Annu. Rev. Immunol., 2:283-318). IFN-γ and M-CSF expression is minimal during biofilm infections (Thurlow, et al. (2011) J. Immunol., 186(11):6585-6596). The amount of IFN-γ and M-CSF used for bioprinting in 3D scaffolds was 100 μg/ml (Adams, et al. (1984) Annu. Rev. Immunol., 2:283-318). 3D scaffolds contained a standard antibiotic cocktail (daptomycin and rifampin; ~8 μg and 3 μg/mg per scaffold, respectively). For both treatment paradigms, mice received 3D scaffolds that are empty (control), antibiotic only (daptomycin and rifampin; ~8 μg and 3 μg/mg per scaffold, respectively), IFN-γ and M-CSF alone, or antibiotic+IFN-γ and M-CSF. 3D bioprinted scaffolds containing macrophage-activating cytokines, antibiotics, or both were placed at day 7 following S. aureus craniotomy infection, whereupon bacterial burdens in the brain were determined 3 and 7 days later (i.e. days 10 and 14 post-infection). Empty scaffolds were included as a control to assess the therapeutic efficacy of the various 3D bioprinted scaffolds. The data indicate that the combination antibiotic and cytokine 3D scaffold formulation enhances biofilm clearance in the brain compared either alone (FIG. 17).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A three-dimensional printed scaffold, wherein said scaffold comprises at least one biocompatible polymer and at least one antibiotic, wherein said scaffold is coated with a hydrogel, and wherein said hydrogel comprises macrophage.

2. The scaffold of claim 1, wherein said scaffold comprises a hydrophobic polymer and a hydrophilic polymer.

3. The scaffold of claim 2, wherein said hydrophobic polymer comprises a hydrophobic antibiotic and said hydrophilic polymer comprises a hydrophilic antibiotic.

4. The scaffold of claim 3, wherein said hydrophobic antibiotic is rifampin and/or said hydrophilic antibiotic is daptomycin.

5. The scaffold of claim 2, wherein said hydrophobic polymer comprises polycaprolactone and/or said hydrophilic polymer comprises hyaluronic acid and/or gelatin.

6. The scaffold of claim 1, wherein said scaffold is mineralized.

7. The scaffold of claim 1, wherein said scaffold comprises hydroxyapatite.

8. The scaffold of claim 1, wherein said scaffold is cross-linked.

9. The scaffold of claim 1, wherein said hydrogel comprises gelatin, optionally with hyaluronic acid, or alginate.

10. The scaffold of claim 1, wherein said macrophage are autologous or allogenic.

11. The scaffold of claim 1, wherein said macrophage are pro-inflammatory.

12. The scaffold of claim 1, wherein said scaffold and/or hydrogel comprises at least one cytokine.

13. The scaffold of claim 12, wherein said cytokine is pro-inflammatory.

14. The scaffold of claim 13, wherein said pro-inflammatory cytokine is macrophage colony stimulating factor and/or IFN-γ.

15. The scaffold of claim 1, wherein the hydrogel further comprises an antibiotic.

16. The scaffold of claim 15, wherein the antibiotic within the hydrogel is contained within microspheres.

17. The scaffold of claim 15, wherein the antibiotic is covalently attached to the hydrogel via a linker.

18. The scaffold of claim 1, wherein the hydrogel comprises covalently attached azide functional groups, optionally via a linker.

19. The scaffold of claim 1, wherein said scaffold is designed to fit within a cranial cavity.

20. The scaffold of claim 1, wherein said scaffold is designed to fit within a cranial cavity, wherein said scaffold comprises a hydrophobic polymer and a hydrophilic polymer, wherein said hydrophobic polymer comprises a hydrophobic antibiotic and said hydrophilic polymer comprises a hydrophilic antibiotic, and wherein said hydrogel comprises macrophage, cytokines, and/or antibiotics.

21. A composition comprising the scaffold of claim 1 and a pharmaceutically acceptable carrier.

22. A three-dimensional printed scaffold, wherein said scaffold comprises at least one biocompatible polymer and at least one antibiotic, wherein said scaffold is coated with a hydrogel, and wherein the hydrogel comprises covalently attached azide functional groups, optionally via a linker.

23. The scaffold of claim 22, wherein said scaffold comprises a hydrophobic polymer and a hydrophilic polymer.

24. The scaffold of claim 23, wherein said hydrophobic polymer comprises a hydrophobic antibiotic and said hydrophilic polymer comprises a hydrophilic antibiotic.

25. The scaffold of claim 22, wherein said hydrophobic polymer comprises polycaprolactone and/or said hydrophilic polymer comprises hyaluronic acid and/or gelatin.

26. The scaffold of claim 25, wherein said hydrophobic antibiotic is rifampin and/or said hydrophilic antibiotic is daptomycin.

27. The scaffold of claim 22, wherein said scaffold is mineralized.

28. The scaffold of claim 22, wherein said scaffold comprises hydroxyapatite.

29. The scaffold of claim 22, wherein said scaffold is cross-linked.

30. The scaffold of claim 22, wherein said hydrogel comprises gelatin, optionally with hyaluronic acid, or alginate.

31. The scaffold of claim 22, wherein said hydrogel comprises macrophage.

32. The scaffold of claim 31, wherein said macrophage are autologous or allogenic.

33. The scaffold of claim 22, wherein said macrophage are pro-inflammatory.

34. The scaffold of claim 22, wherein said scaffold and/or hydrogel comprises at least one cytokine.

35. The scaffold of claim 34, wherein said cytokine is pro-inflammatory.

36. The scaffold of claim 35, wherein said pro-inflammatory cytokine is macrophage colony stimulating factor and/or IFN-γ.

37. The scaffold of claim 22, wherein the hydrogel further comprises an antibiotic.

38. The scaffold of claim 37, wherein the antibiotic within the hydrogel is contained within microspheres.

39. The scaffold of claim 37, wherein the antibiotic is covalently attached to the hydrogel via a linker.

40. The scaffold of claim 22, wherein said scaffold is designed to fit within a cranial cavity.

41. The scaffold of claim 22, wherein said scaffold is designed to fit within a cranial cavity, wherein said scaffold comprises a hydrophobic polymer and a hydrophilic polymer, wherein said hydrophobic polymer comprises a hydrophobic antibiotic and said hydrophilic polymer comprises a hydrophilic antibiotic, and wherein said hydrogel comprises macrophage, cytokines, and/or antibiotics.

42. A composition comprising the scaffold of claim 22 and a pharmaceutically acceptable carrier.

\* \* \* \* \*